(12) United States Patent
Porter et al.

(10) Patent No.: US 10,501,782 B1
(45) Date of Patent: Dec. 10, 2019

(54) CELL-FREE SYNTHESIS OF DNA BY STRAND DISPLACEMENT

(71) Applicant: Touchlight IP Limited, London (GB)

(72) Inventors: Neil Porter, London (GB); Paul Rothwell, London (GB); Jonathan Extance, London (GB)

(73) Assignee: Touchlight IP Limited, London (GB)

( * ) Notice: Subject to any disclaimer, the term of this patent is extended or adjusted under 35 U.S.C. 154(b) by 0 days.

(21) Appl. No.: 15/508,766

(22) PCT Filed: Aug. 21, 2015

(86) PCT No.: PCT/GB2015/052434
§ 371 (c)(1),
(2) Date: Mar. 3, 2017

(87) PCT Pub. No.: WO2016/034849
PCT Pub. Date: Mar. 10, 2016

(30) Foreign Application Priority Data

Sep. 5, 2014 (GB) .................................. 1415789.5

(51) Int. Cl.
*C12P 19/34* (2006.01)
*C12Q 1/6844* (2018.01)
(52) U.S. Cl.
CPC .................................. *C12Q 1/6844* (2013.01)
(58) Field of Classification Search
None
See application file for complete search history.

(56) References Cited

U.S. PATENT DOCUMENTS

| 5,720,923 A | 2/1998 | Haff et al. |
| 5,922,591 A | 7/1999 | Anderson et al. |
| 8,163,489 B2 | 4/2012 | Murray et al. |
| 2003/0235844 A1 | 12/2003 | Slepnev |
| 2007/0190641 A1 | 8/2007 | Wilding et al. |
| 2012/0052560 A1 | 3/2012 | Knight et al. |
| 2013/0216562 A1* | 8/2013 | Porter .................. C12Q 1/6846 424/184.1 |

FOREIGN PATENT DOCUMENTS

| RU | 2218414 C2 | 12/2003 |
| WO | WO 99/33559 | 7/1999 |
| WO | WO 03/035841 | 5/2003 |
| WO | WO 2004/007684 | 1/2004 |
| WO | WO 2004/074503 | 9/2004 |
| WO | 2006/119066 A2 | 11/2006 |
| WO | 2012/017210 A1 | 2/2012 |

OTHER PUBLICATIONS

Heinrich et al. "Linear closed mini DNA generated by the prokaryotic cleaving-joining enzyme TelN is functional in mammalian cells", Journal of Molecular Medicine, vol. 80, No. 10, Oct. 1, 2002, pp. 648-654.
Lee, et al. "Simulation and real-time monitoring of polymerase chain reaction for its higher efficiency", Biochemical Engineering Journal, 2006, vol. 29, pp. 109-118.

* cited by examiner

*Primary Examiner* — Kenneth R Horlick
(74) *Attorney, Agent, or Firm* — Norton Rose Fulbright US LLP

(57) ABSTRACT

The present invention relates to an improved process for synthesis of DNA, RNA, proteins and like molecules, in particular cell-free enzymatic synthesis of DNA, preferably in large scale. The present invention relates to the synthesis of DNA using strand-displacement replication and the addition of nucleotides to the reaction mixture is controlled, thus controlling yield. The reaction mixture contains a starting amount of nucleotides, polymerase and DNA template, to which further nucleotides are supplied in a controlled manner.

31 Claims, 10 Drawing Sheets

CELL-FREE SYNTHESIS OF DNA BY STRAND DISPLACEMENT

CROSS-REFERENCE TO RELATED APPLICATIONS

This application is a national phase application under 35 U.S.C. § 371 that claims priority to International Application No. PCT/GB2015/052434 filed on Aug. 21, 2015, which claims the benefit of Great Britain Application No. 1415789.5 filed Sep. 5, 2014, both of which are incorporated herein by reference in their entirety.

FIELD

The present invention relates to an improved process for synthesis of DNA, RNA, proteins and like molecules, in particular cell-free enzymatic synthesis of DNA, preferably in large scale.

BACKGROUND

Amplification of deoxyribonucleic acid (DNA) may be carried out through use of cell-based processes, such as by culture of bacteria propagating a DNA to be amplified in fermenters. Cell-free enzymatic processes for amplification of DNA from a starting template have also been described, including the polymerase chain reaction and strand-displacement reactions.

In the past, amplification of DNA on a test scale has been performed using apparatus based on microtitre plates and robotically controlled pipettes to add reaction components as required. Such apparatus and processes are suitable for manufacturing small quantities of DNA molecules for test purposes but do not provide sufficient quantities for other purposes. Large scale amplification and manufacture of specific nucleic acids and proteins has mostly been carried out through cell-based processes. Such methods are generally effective for production of very large volumes of product but costly to set up.

There are also many apparatus available that are specifically adapted to amplify DNA samples using the thermocyclic method to effect the polymerase chain reaction (PCR). These apparatus are ideally suited to that reaction but are inflexible and cannot be adapted to perform other reactions. An example of such an apparatus is disclosed in U.S. Pat. No. 8,163,489.

Large-scale DNA synthesis using chemical synthesis, such as phosphoramidite methods, are known, but are not without drawbacks. The reaction must generally be performed in organic solvents, many of which are toxic or otherwise hazardous. Another drawback to chemical synthesis is that it is not completely efficient, since following each nucleotide addition, at least 2 percent of the growing oligonucleotide chains are capped, resulting in a yield loss. The total yield loss for the nucleotide chain being synthesised thus increases with each nucleotide added to the sequence. This inherent inefficiency in chemical synthesis of oligonucleotides ultimately limits the length of oligonucleotide that can be efficiently produced to oligonucleotides having 50 nucleic acid residues or less.

To date, biological catalysts such as polymerase have not been routinely exploited for industrial scale manufacture of DNA products and reactions have largely been limited to volumes at microliter scale. Scaling up processes using enzymatic synthesis of DNA has proved problematic, not least with the disappointing yield of DNA product.

There is therefore a need for a process that can be used to synthesise DNA and like molecules at significant scale.

SUMMARY

The present invention relates to a process for cell-free production of DNA. The process may allow for enhanced production of DNA compared to current methodologies involving closed batch processes. This significantly increases productivity whilst reducing the cost of synthesising DNA, particularly on a large scale. The present invention relates generally to isothermal methods of amplifying DNA that do not require temperature to be cycled via heating and cooling.

Accordingly there is provided a cell-free process for synthesising DNA comprising contacting a DNA template with at least one polymerase in the presence of one or more primers and nucleotides to form a reaction mixture, under conditions promoting amplification of said template by displacement of replicated strands through strand-displacement replication of another strand, wherein further nucleotides are supplied in a controlled manner to the reaction mixture.

The cell-free process thus involves amplification of the template via strand displacement replication. There is provided a cell-free process for synthesising DNA comprising contacting a DNA template with at least one polymerase in the presence of one or more primers and nucleotides to form a reaction mixture, under conditions promoting amplification of said template by strand displacement replication, wherein further nucleotides are supplied in a controlled manner to the reaction mixture Accordingly there is also provided a cell-free process for synthesising DNA comprising contacting a DNA template with at least one polymerase in the presence of nucleotides to form a reaction mixture, under conditions promoting amplification of said template by displacement of replicated strands through strand-displacement replication of another strand, wherein further nucleotides are supplied in a controlled manner to the reaction mixture.

The cell-free process thus involves amplification of the template via strand displacement replication. There is provided a cell-free process for synthesising DNA comprising contacting a DNA template with at least one polymerase in the presence of nucleotides to form a reaction mixture, under conditions promoting amplification of said template by strand displacement replication, wherein further nucleotides are supplied in a controlled manner to the reaction mixture.

Thus, the provision of a controlled supply of further nucleotides to the reaction mixture is advantageous, since this rational control strategy can allow for improvements in the rate of synthesis of the DNA and/or an improved DNA yield. These improvements are compared to an analogous reaction mixture where all the nucleotides are supplied in the reaction mixture at the start. The controlled supply of further nucleotides may allow for increased productivity and/or processivity of the polymerase enzyme.

Alternatively, there is provided a cell-free process for synthesising DNA comprising contacting a DNA template with at least one polymerase in the presence of one or more primers, nucleotides and metal cations to form a reaction mixture, under conditions promoting amplification of said template by displacement of replicated strands through strand-displacement replication of another strand, wherein further metal cations are supplied in a controlled manner to the reaction mixture.

The cell-free process thus involves amplification of the template via strand displacement replication. There is provided a cell-free process for synthesising DNA comprising contacting a DNA template with at least one polymerase in the presence of one or more primers, nucleotides and metal cations to form a reaction mixture, under conditions promoting amplification of said template by strand displacement replication, wherein further metal ions are supplied in a controlled manner to the reaction mixture.

Alternatively, there is provided a cell-free process for synthesising DNA comprising contacting a DNA template with at least one polymerase in the presence of nucleotides and metal cations to form a reaction mixture, under conditions promoting amplification of said template by displacement of replicated strands through strand-displacement replication of another strand, wherein further metal cations are supplied in a controlled manner to the reaction mixture.

The cell-free process thus involves amplification of the template via strand displacement replication. There is provided a cell-free process for synthesising DNA comprising contacting a DNA template with at least one polymerase in the presence of nucleotides and metal cations to form a reaction mixture, under conditions promoting amplification of said template by strand displacement replication, wherein further metal ions are supplied in a controlled manner to the reaction mixture Thus, the provision of a controlled supply of further metal cations to the reaction mixture is advantageous, since this rational control strategy can allow for improvements in the rate of synthesis of the DNA. These improvements are compared to an analogous reaction mixture where all the metal cations are supplied in the reaction mixture at the start. The controlled supply of further metal cations may allow for increased productivity and/or processivity of the polymerase enzyme.

There is also provided a cell-free process for synthesising DNA comprising contacting a DNA template with at least one polymerase in the presence of one or more primers, nucleotides and metal cations to form a reaction mixture, under conditions promoting amplification of said template by displacement of replicated strands through strand-displacement replication of another strand, wherein further nucleotides and metal cations are supplied in a controlled manner to the reaction mixture.

The cell-free process thus involves amplification of the template via strand displacement replication. There is provided a cell-free process for synthesising DNA comprising contacting a DNA template with at least one polymerase in the presence of one or more primers, nucleotides and metal ions to form a reaction mixture, under conditions promoting amplification of said template by strand displacement replication, wherein further nucleotides and further metal cations are supplied in a controlled manner to the reaction mixture.

There is also provided a cell-free process for synthesising DNA comprising contacting a DNA template with at least one polymerase in the presence of nucleotides and metal cations to form a reaction mixture, under conditions promoting amplification of said template by displacement of replicated strands through strand-displacement replication of another strand, wherein further nucleotides and metal cations are supplied in a controlled manner to the reaction mixture.

The cell-free process thus involves amplification of the template via strand displacement replication. There is provided a cell-free process for synthesising DNA comprising contacting a DNA template with at least one polymerase in the presence of nucleotides and metal ions to form a reaction mixture, under conditions promoting amplification of said template by strand displacement replication, wherein further nucleotides and further metal cations are supplied in a controlled manner to the reaction mixture.

The further nucleotides and further metal cations may be supplied together or separately. It is preferred that the nucleotides and metal ions are not mixed together prior to being supplied to the reaction mixture. The further nucleotides and further metal cations may be added as each are required to the reaction mixture independently of each other.

Thus, the provision of a controlled supply of further nucleotides and further metal cations to the reaction mixture is advantageous, since this rational control strategy can allow for improvements in the rate of synthesis of the DNA and/or an improved DNA yield. These improvements are compared to an analogous reaction mixture where all the nucleotides and metal cations are supplied in the reaction mixture at the start. The controlled supply of further nucleotides may allow for increased productivity and/or processivity of the polymerase enzyme.

According to each of several further aspects of the invention, there is provided apparatus configured to perform a process according to the first, second or third aspect of the present invention. The apparatus may be used to perform a process according to any aspect of the invention.

According to a further aspect of the invention, the DNA template may comprise one or more processing enzyme target sites. The reaction mixture may be contacted at any time with one or more processing enzymes. Said enzymes may be provided to said reaction mixture in a controlled manner. Preferably, the processing enzyme is a protelomerase enzyme.

Independently, optional features of any aspect of the invention may be: The DNA template may be circular. The strand displacement amplification of said DNA template may be carried out by rolling circle amplification (RCA). The DNA polymerase may be Phi29 or a variant thereof. The amplification of DNA may be isothermal amplification. The one or more primers may be random primers. The synthesised DNA may comprise concatamers comprising tandem units of DNA sequence amplified from the DNA template. The DNA template may be a closed linear DNA; preferably the DNA template is incubated under denaturing conditions to form a closed circular single stranded DNA. The DNA template may comprise at least one processing enzyme target sequence, preferably a recombinase target sequence or a protelomerase target sequence. The DNA template may comprise an expression cassette comprising a eukaryotic promoter operably linked to a coding sequence of interest, and optionally a eukaryotic transcription termination sequence. The expression cassette may be flanked on either side by a processing enzyme target sequence, preferably a recombinase targeting sequence or a protelomerase target sequence. The amplified DNA may be contacted with a recombinase enzyme or a protelomerase enzyme, as appropriate.

The quantity of DNA that may be synthesised is equal to or higher than 1 gram per litre of reaction mixture.

The further nucleotides and/or further metal ions may be supplied in a plurality of aliquots to the reaction mixture. The further nucleotides and/or further metal ions may be supplied at regular intervals throughout the duration of the process, optionally at least every 30 minutes. At least 3, 4, 5, 6, 7, 8, 9 or 10 aliquots may be supplied to the reaction mixture. The further nucleotides and/or further metal ions may be supplied in a continuous manner to the reaction mixture. The further metal ions and/or further nucleotides may be fed into the reaction mixture, optionally from an external source using a pump or are supplied to the reaction mixture by use of an osmotic pump.

The nucleotides or further nucleotides may comprise biologically inactive nucleotides; optionally these biologically inactive nucleotides are supplied to the reaction mixture via activation, preferably by a chemical or physical means. The biologically inactive nucleotides may be caged nucleotides that are activated by photolysis.

The further nucleotides and/or further metal ions and/or processing enzyme may be supplied in response to a signal related to the concentration of DNA in the reaction mixture, which may be optionally monitored by measuring the difference in pressure of the reaction mixture, or a portion thereof, which may possibly generate a signal. The signal indicating the concentration of DNA may be generated by measuring a pressure difference created by a reciprocating pump that removes and returns a portion of the reaction mixture, optionally over a pressure sensor.

The metal cations or further metal cations may comprise one or more metals selected from the list consisting of: $Mg^{2+}$, $Be^{2+}$, $Ca^{2+}$, $Sr^{2+}$, $Li^+$, $Na^+$, $K^+$, $Mn^{2+}$ or $Zn^{2+}$, preferably $Mg^{2+}$. The further metal cations may be supplied with the further nucleotides. The ratio between the metal cations and the nucleotides may be maintained at about 3:1 in the reaction mixture. The concentration of metal ions discussed herein, particularly the free metal ion concentration, relates to the specific metal cation of interest (i.e. $Mg^{2+}$) and not the concentration of all species of metal ions in the reaction mixture.

The reaction mixture may contain at least one nucleotide. One or more further nucleotides may then be added. The nucleotides or further nucleotides are deoxyribonucleoside triphosphates (dNTPs), or a derivative or modified version thereof. The nucleotides or further nucleotides are one or more of deoxyadenosine triphosphate (dATP), deoxyguanosine triphosphate (dGTP), deoxycytidine triphosphate (dCTP), deoxythymidine triphosphate (dTTP) and derivatives thereof. The nucleotides or further nucleotides are provided as one or more of free acids, their salts or chelates thereof. The salts or chelates may include one or more of the following metal ions: $Mg^{2+}$, $Be^{2+}$, $Ca^{2+}$, $Sr^{2+}$, $Li^+$, $Na^+$, $K^+$, $Mn^{2+}$ or $Zn^{2+}$. The concentration of nucleotides in the reaction mixture may be maintained between 0.001 mM and 6 mM, optionally at about 3 mM.

The process may be a batch process or a continuous flow process. Further optional features are as described in the dependent claims.

Further advantages are described below.

BRIEF DESCRIPTION OF THE DRAWINGS

The present invention will be described further below with reference to exemplary embodiments and the accompanying drawings, in which.

DETAILED DESCRIPTION

Figure 1:
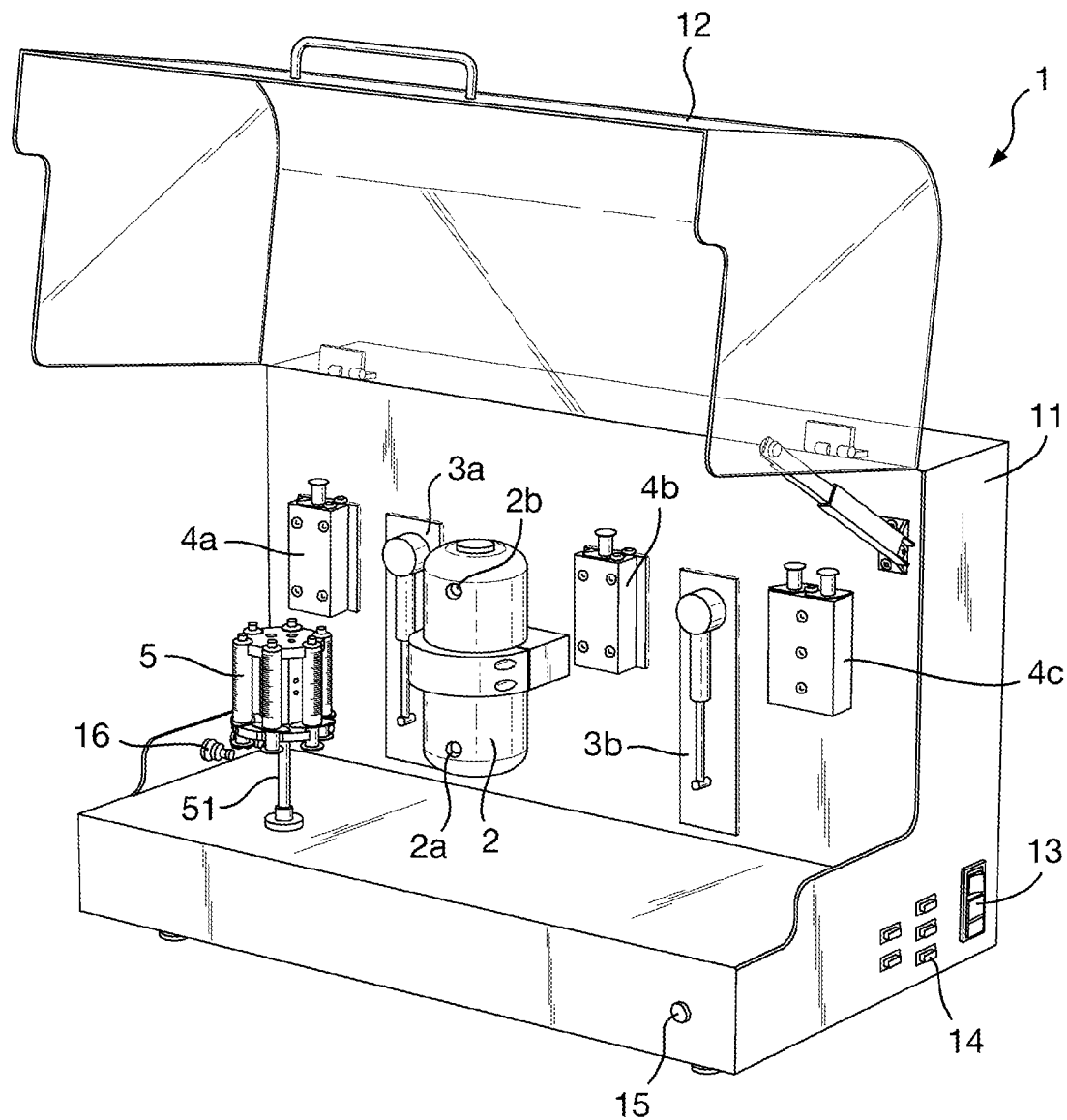
FIG. 1 is a perspective view of a synthesis apparatus useful according to an embodiment of the invention. For ease of understanding and to make the main components more visible, certain components and connecting conduits are omitted in this Figure.

The present invention relates to cell-free processes for synthesising DNA. The processes of the invention may allow for a high throughput synthesis of DNA.

The deoxyribonucleic acid (DNA) synthesised according to the present invention can be any DNA molecule. The DNA may be single stranded or double stranded. The DNA may be linear. The DNA may be processed to form circles, particularly minicircles, single stranded closed circles, double stranded closed circles, double stranded open circles, or closed linear double stranded DNA. The DNA may be allowed to form, or processed to form a particular secondary structure, such as, but not limited to hairpin loops (stem loops), imperfect hairpin loops, pseudoknots, or any one of the various types of double helix (A-DNA, B-DNA, or Z-DNA). The DNA may also form hairpins.

The DNA synthesised may be of any suitable length. Lengths of up to or exceeding 77 kilobases (kb or kbase) may be possible using the process of the invention. More particularly, the length of DNA which may be synthesised according to the process may be in the order of up to 60 kilobases, or up to 50 kilobases, or up to 40 kilobases, or up to 30 kilobases. Preferably the DNA synthesised may be 100 bases to 60 kilobases, 200 bases to 20 kilobases, more preferably 200 bases to 15 kilobases, most preferably 2 kilobases to 15 kilobases.

The amount of DNA synthesised according to the processes of the present invention may exceed 10 g/l of reaction mixture. It is preferred that the amount of DNA synthesised is up to 10, 9, 8, 7, 6 or 5 g/l. A preferred amount of DNA synthesized is 0.2 to 5 g/l, preferably 1 to 5 g/l. The amount of DNA produced may be described as industrial or commercial quantities, on a large-scale, or mass production. The DNA produced by the processes may be uniform in quality, namely in DNA length and sequence. The processes may thus be suitable for large scale synthesis of DNA.

In currently available techniques of synthesising DNA, most are on a small or lab-based scale, the reactions taking place in microliter volumes. Efforts to scale-up PCR, still result in poor yields of DNA, such as approximately 20-40 mg per litre of reaction mixture (Vandalia), since the reaction is taking place only with a starting amount of nucleotides, and no further nucleotides are supplied, and the product formation inhibits the reaction.

The DNA template may be any suitable template. The DNA template may be single stranded (ss) or double stranded (ds). The DNA template may be linear or circular. A double stranded DNA template may be an open circular ds DNA, a closed circular ds DNA, an open linear ds DNA or a closed linear ds DNA. A single stranded DNA template may be a linear ss DNA or a closed circular ss DNA. The latter DNA template can be produced by denaturing a closed linear ds DNA. Closed linear DNA, i.e. linear ds covalently closed DNA molecules, typically comprise covalently closed ends, i.e. hairpin ends, where base pairing between complementary DNA strands is not present. The hairpin loops join the ends of complementary DNA strands. The loops may themselves contain complementary sequences, particularly if the loops comprise part of the protelomerase target sequence. The closed linear ds DNA may be a plasmid.

The DNA template may comprise any sequence, either naturally derived or artificial. The DNA template may comprise at least one processing enzyme target sequence, such as one, two, three, four or more processing enzyme target sites. Such a target sequence is to allow for the DNA to be optionally processed further following synthesis. A processing enzyme is an enzyme that recognises its target site and processes the DNA. The processing enzyme target sequence may be a target sequence for a restriction enzyme. A restriction enzyme, i.e. a restriction endonuclease, binds to a target sequence and cleaves at a specific point. The processing enzyme target sequence may be a target for a recombinase. A recombinase directionally catalyses a DNA exchange reactions between short (30-40 nucleotides) target site sequences that are specific to each recombinase. Examples of recombinases include the Cre recombinase (with loxP as a target sequence) and FLP recombinase (with short flippase recognition target (FRT) sites). The processing enzyme target sequence may be a target for a site-specific integrase, such as the phiC31 integrase. The processing enzyme target sequence may be a target for a protelomerase enzyme. A protelomerase target sequence is any DNA sequence whose presence in a DNA template allows for its conversion into a closed linear DNA by the enzymatic activity of protelomerase. In other words, the protelomerase target sequence is required for the cleavage and religation of double stranded DNA by protelomerase to form covalently closed linear DNA. Typically, a protelomerase target sequence comprises any palindromic sequence i.e. any double-stranded DNA sequence having two-fold rotational symmetry, also described herein as an inverted repeat. The length of the inverted repeat differs depending on the specific organism. The palindrome or inverted repeat may be perfect or imperfect. A protelomerase target sequence preferably comprises a double stranded palindromic (inverted repeat) sequence of at least 14 base pairs in length. Suitable protelomerase targeting sites are known in the art and discussed in EP2,391,731, incorporated herein by reference. A suitable protelomerase enzyme may be TelN from the *Escherichia coli* phage N15. It is preferred that the processing enzyme target site is a protelomerase targeting site.

The processing enzyme target sequence may be a target sequence for a RNA polymerase, such that the DNA becomes a template for polypeptide synthesis. In this instance, the processing enzyme targeting site is a promoter, preferably a eukaryotic promoter.

The process may comprise an additional step of contacting the reaction mixture with a processing enzyme. The reaction mixture can be contacted with a processing enzyme at any time. Preferably, the reaction mixture is contacted with a processing enzyme once DNA synthesis is complete. The processing enzyme may be a RNA polymerase, a recombinase, a restriction endonuclease or a protelomerase. Preferably the processing enzyme is a protelomerase.

A protelomerase, as may be used in the invention, is any polypeptide capable of cleaving and rejoining a template comprising a protelomerase target site in order to produce a covalently closed linear DNA molecule. Thus, the protelomerase has DNA cleavage and ligation functions. Enzymes having protelomerase-type activity have also been described as telomere resolvases (for example in *Borrelia burgdorferi*). A typical substrate for protelomerase is circular double stranded DNA. If this DNA contains a protelomerase target site, the enzyme can cut the DNA at this site and ligate the ends to create a linear double stranded covalently closed DNA molecule. The requirements for protelomerase target sites are discussed above. As also outlined above, the ability of a given polypeptide to catalyse the production of closed linear DNA from a template comprising a protelomerase target site can be determined using any suitable assay described in the art.

The processing of DNA may require the use of at least one protelomerase. The process of the invention may comprise use of more than one protelomerase, such as two, three, four, five or more different protelomerases. Examples of suitable protelomerases include those from bacteriophages such as phiHAP-1 from *Halomonas quamarina*, PY54 from *Yersinia enterolytica* phiK02 from *Klebsiella oxytoca* and VP882 from *Vibrio* sp., and N15 from *Escherichia coli* (SEQ ID NO: 15), or variants of any thereof. Use of bacteriophage N15 protelomerase or a variant thereof is particularly preferred. This enzyme is also referred to as TelN. These enzymes are further described in WO2012/017210, incorporated herein by reference.

The process may thus be performed on a DNA template that includes a processing enzyme, and the processing enzyme may be supplied in a controlled manner to the reaction mixture. The processing enzyme may be supplied at any appropriate time to the reaction mixture; this may be in response to a signal. One or more additions of processing enzyme may be made. It is preferred that the processing enzyme is supplied in aliquots, which are added discretely to the reaction mixture. 1, 2, 3, 4, 5, 6, 7, 8, 9, 10 or more aliquots of processing enzyme may be added to the reaction mixture. It may be advantageous to add the processing enzyme just before an aliquot of further nucleotides and/or further metal ions are required. Alternatively, the processing enzyme may be added with or after an aliquot of further nucleotides are added to the reaction mixture. The processing enzyme may be added in response to a signal that the DNA in the reaction mixture has reached a desired concentration. This concentration of DNA may be detected as described herein.

The DNA template may comprise an expression cassette comprising, consisting or consisting essentially of a eukaryotic promoter operably linked to a sequence enclosing a protein of interest, and optionally a eukaryotic transcription termination sequence. Optionally the expression cassette may be a minimal cassette, which lacks one or more bacterial or vector sequences, typically selected from the group consisting of: (i) bacterial origins of replication; (ii) bacterial selection markers (such as antibiotic resistance genes), and (iii) unmethylated CpG motifs. A "promoter" is a nucleotide sequence which initiates and regulates transcription of a polynucleotide. Promoters can include inducible promoters (where expression of a polynucleotide sequence operably linked to the promoter is induced by an analyte, co factor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions. "Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence. Thus, the term "operably linked" is intended to encompass any spacing or orientation of the promoter element and the DNA sequence of interest which allows for initiation of transcription of the DNA sequence of interest upon recognition of the promoter element by a transcription complex.

The DNA template may be of any suitable length. Particularly, the DNA template may be up to 60 kilobases, or up to 50 kilobases, or up to 40 kilobases, or up to 30 kilobases. Preferably the DNA template may be 100 bases to 60 kilobases, 200 bases to 20 kilobases, more preferably 200 bases to 15 kilobases, most preferably 2 kilobases to 15 kilobases.

The DNA template may be provided in an amount sufficient for use in the process by any method known in the art. For example, the template may be produced by PCR.

The whole or a selected portion of the DNA template may be amplified in the process.

The DNA template may comprise a DNA sequence for expression. The DNA may be for expression in a cell (i.e. a transfected cell in vitro or in vivo), or may be for expression in a cell free system (i.e. protein synthesis). The DNA sequence for expression may be for therapeutic purposes, i.e. gene therapy of a DNA vaccine. The sequence for expression may be a gene, and said gene may encode a DNA vaccine, a therapeutic protein and the like. The DNA sequence may comprise a sequence which is transcribed into an active RNA form, i.e. a small interfering RNA molecule (siRNA).

The DNA template is contacted with at least one polymerase. One, two, three, four or five different polymerases may be used. The polymerase may be any suitable polymerase, such that it synthesises polymers of DNA. The polymerase may be a DNA polymerase. Any DNA polymerase may be used, including any commercially available DNA polymerase. Two, three, four, five or more different DNA polymerases may be used, for example one which provides a proofreading function and one or more others which do not. DNA polymerases having different mechanisms may be used e.g. strand displacement type polymerases and DNA polymerases replicating DNA by other methods. A suitable example of a DNA polymerase that does not have strand displacement activity is T4 DNA polymerase.

A polymerase may be highly stable, such that its activity is not substantially reduced by prolonged incubation under process conditions. Therefore, the enzyme preferably has a long half-life under a range of process conditions including but not limited to temperature and pH. It is also preferred that a polymerase has one or more characteristics suitable for a manufacturing process. The polymerase preferably has high fidelity, for example through having proofreading activity. Furthermore, it is preferred that a polymerase displays high processivity, high strand-displacement activity and a low Km for dNTPs and DNA. A polymerase may be capable of using circular and/or linear DNA as template. The polymerase may be capable of using dsDNA or ssDNA as a template. It is preferred that a polymerase does not display DNA exonuclease activity that is not related to its proofreading activity.

The skilled person can determine whether or not a given polymerase displays characteristics as defined above by comparison with the properties displayed by commercially available polymerases, e.g. Phi29 (New England Biolabs, Inc., Ipswich, Mass., US), Deep Vent® (New England Biolabs, Inc.), *Bacillus stearothermophilus* (Bst) DNA polymerase I (New England Biolabs, Inc.), Klenow fragment of DNA polymerase I (New England Biolabs, Inc.), M-MuLV reverse transcriptase (New England Biolabs, Inc.), VentR® (exo-minus) DNA polymerase (New England Biolabs, Inc.), VentR® DNA polymerase (New England Biolabs, Inc.), Deep Vent® (exo-) DNA polymerase (New England Biolabs, Inc.) and Bst DNA polymerase large fragment (New England Biolabs, Inc.). Where a high processivity is referred to, this typically denotes the average number of nucleotides added by a polymerase enzyme per association/dissociation with the template, i.e. the length of primer extension obtained from a single association event.

Strand displacement-type polymerases are preferred. Preferred strand displacement-type polymerases are Phi 29, Deep Vent and Bst DNA polymerase I or variants of any thereof. "Strand displacement" describes the ability of a polymerase to displace complementary strands on encountering a region of double stranded DNA during synthesis. The template is thus amplified by displacing complementary strands and synthesizing a new complementary strand. Thus, during strand displacement replication, a newly replicated strand will be displaced to make way for the polymerase to replicate a further complementary strand. The amplification reaction initiates when a primer or the 3' free end of a single stranded template anneals to a complementary sequence on a template (both are priming events). When DNA synthesis proceeds and if it encounters a further primer or other strand annealed to the template, the polymerase displaces this and continues its strand elongation. The strand displacement generates newly synthesised single stranded DNA which can act as a template for more priming events. The priming of the newly synthesised DNA leads to hyper-branching, and a high yield of products. It should be understood that strand displacement amplification methods differ from PCR-based methods in that cycles of denaturation are not essential for efficient DNA amplification, as double-stranded DNA is not an obstacle to continued synthesis of new DNA strands. Strand displacement amplification may only require one initial round of heating, to denature the initial template if it is double stranded, to allow the primer to anneal to the primer binding site if used. Following this, the amplification may be described as isothermal, since no further heating or cooling is required. In contrast, PCR methods require cycles of denaturation (i.e. elevating temperature to 94 degrees centigrade or above) during the amplification process to melt double-stranded DNA and provide new single stranded templates. During strand displacement, the polymerase will displace strands of already synthesised DNA. Further, it will use newly synthesised DNA as a template, ensuring rapid amplification of DNA.

A strand displacement polymerase used in the process of the invention preferably has a processivity of at least 20 kb, more preferably, at least 30 kb, at least 50 kb, or at least 70 kb or greater. In one embodiment, the strand displacement DNA polymerase has a processivity that is comparable to, or greater than phi29 DNA polymerase.

Strand displacement replication is, therefore, preferred. During strand displacement replication, the template is amplified by displacing already replicated strands, which have been synthesised by the action of the polymerase, in turn displacing another strand, which can be the original complementary strand of a double stranded template, or a newly synthesised complementary strand, the latter synthesised by the action of a polymerase on an earlier primer annealed to the template. Thus, the amplification of the template may occur by displacement of replicated strands through strand displacement replication of another strand. This process may be described as strand displacement amplification or strand displacement replication.

A preferred strand displacement replication process is Loop-mediated isothermal amplification, or LAMP. LAMP generally uses 4-6 primers recognizing 6-8 distinct regions of the template DNA. In brief, a strand-displacing DNA polymerase initiates synthesis and 2 of the primers form loop structures to facilitate subsequent rounds of amplification. An inner primer containing sequences of the sense and antisense strands of the target DNA initiates LAMP. The following strand displacement DNA synthesis primed by an outer primer releases a single-stranded DNA. This serves as template for DNA synthesis primed by the second inner and outer primers that hybridise to the other end of the target, which produces a stem-loop DNA structure. In subsequent LAMP cycling one inner primer hybridises to the loop on the product and initiates displacement DNA synthesis, yielding the original stem-loop DNA and a new stem-loop DNA with a stem twice as long.

A preferred strand displacement replication process is rolling circle amplification (RCA). The term RCA describes the ability of RCA-type polymerases to continuously progress around a circular DNA template strand whilst extending a hybridised primer. This leads to formation of linear single stranded products with multiple repeats of amplified DNA. The sequence of the circular template (a single unit) is multiply repeated within a linear product. For a circular template, the initial product of strand displacement amplification is a single stranded concatamer, which is either sense or antisense, depending on the polarity of the template. These linear single stranded products serve as the basis for multiple hybridisation, primer extension and strand displacement events, resulting in formation of concatameric double stranded DNA products, again comprising multiple repeats of amplified DNA. There are thus multiple copies of each amplified "single unit" DNA in the concatameric double stranded DNA products. RCA polymerases are particularly preferred for use in the process of the present invention. The products of RCA-type strand displacement replication processes may require processing to release single unit DNAs. This is desirable if single units of DNA are required.

In order to allow for amplification, the DNA template is also contacted with one or more primers. The primers may be non-specific (i.e. random in sequence) or may be specific for one or more sequences comprised within the DNA template. If the primers are of random sequence they allow for non-specific initiation at any site on the DNA template. This allows for high efficiency of amplification through multiple initiation reactions from each template strand. Examples of random primers are hexamers, heptamers, octamers, nonamers, decamers or sequences greater in length, for example of 12, 15, 18, 20 or 30 nucleotides in length. A random primer may be of 6 to 30, 8 to 30 or 12 to 30 nucleotides in length. Random primers are typically provided as a mix of oligonucleotides which are representative of all potential combinations of e.g. hexamers, heptamers, octamers or nonamers in the DNA template.

In one embodiment, the primers or one or more of the primers are specific. This means they have a sequence which is complementary to a sequence in the DNA template from which initiation of amplification is desired. In this embodiment, a pair of primers may be used to specifically amplify a portion of the DNA template which is internal to the two primer binding sites. Alternatively, a single specific primer may be used.

In one embodiment, the DNA template includes one or more protelomerase target sequences. Such target sequences are palindromic in nature. In this embodiment, it is possible to use a specific primer which binds to the palindromic sequence within a protelomerase binding site, and can thus prime amplification on both strands of the DNA template. Such a process is described in detail in WO2012/017210. Thus, a single primer is sufficient for amplification.

Primers may be unlabelled, or may comprise one or more labels, for example radionuclides or fluorescent dyes. Primers may also comprise chemically modified nucleotides. For example, the primer may be capped in order to prevent initiation of DNA synthesis until the cap is removed, i.e., by chemical or physical means. Primer lengths/sequences may typically be selected based on temperature considerations i.e. as being able to bind to the template at the temperature used in the amplification step.

The contacting of the DNA template with the polymerase and one or more primers may take place under conditions promoting annealing of primers to the DNA template. The conditions include the presence of single-stranded DNA allowing for hybridisation of the primers. The conditions also include a temperature and buffer allowing for annealing of the primer to the template. Appropriate annealing/hybridisation conditions may be selected depending on the nature of the primer. An example of preferred annealing conditions used in the present invention include a buffer 30 mM Tris-HCl pH 7.5, 20 mM KCl, 8 mM $MgCl_2$. The annealing may be carried out following denaturation using heat by gradual cooling to the desired reaction temperature.

However, amplification using strand displacement replication can also take place without a primer, and thus requires no hybridisation and primer extension to occur. Instead, the single stranded DNA template self-primes by forming hairpins, which have a free 3' end available for extension. The remaining steps of the amplification remain the same.

The DNA template and polymerase are also contacted with nucleotides. The combination of DNA template, polymerase and nucleotides forms a reaction mixture. The reaction mixture may also comprise a one or more primers. The reaction mixture may independently also include one or more metal cations.

A nucleotide is a monomer, or single unit, of nucleic acids, and nucleotides are composed of a nitrogenous base, a five-carbon sugar (ribose or deoxyribose), and at least one phosphate group. Any suitable nucleotide may be used.

The nucleotides may be present as free acids, their salts or chelates, or a mixture of free acids and/or salts or chelates.

The nucleotides may be present as monovalent metal ion nucleotide salts or divalent metal ion nucleotide salts. The salts may include salts of divalent metal ions, such as, but not limited to magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), or salts of monovalent metal ions, including but not limited to lithium ($Li^+$), sodium ($Na^+$) or potassium ($K^+$).

The nitrogenous base may be adenine (A), guanine (G), thymine (T), cytosine (C), and uracil (U). The nitrogenous base may also be modified bases, such as 5-methylcytosine (m5C), pseudouridine (ψ), dihydrouridine (D), inosine (I), and 7-methylguanosine (m7G).

It is preferred that the five-carbon sugar is a deoxyribose, such that the nucleotide is a deoxynucleotide.

The nucleotide may be in the form of deoxynucleoside triphosphate, denoted dNTP. This is a preferred embodiment of the present invention. Suitable dNTPs may include dATP (deoxyadenosine triphosphate), dGTP (deoxyguanosine triphosphate), dTTP (deoxythymidine triphosphate), dUTP (deoxyuridine triphosphate), dCTP (deoxycytidine triphosphate), dITP (deoxyinosine triphosphate), dXTP (deoxyxanthosine triphosphate), and derivatives and modified versions thereof. It is preferred that the dNTPs comprise one or more of dATP, dGTP, dTTP or dCTP, or modified versions or derivatives thereof. It is preferred to use a mixture of dATP, dGTP, dTTP and dCTP or modified version thereof.

The nucleotides may be in solution or provided in lyophilised form. A solution of nucleotides is preferred.

The nucleotides may comprise modified nucleotides, and these modified nucleotides may be in a biologically inactive form. The modified nucleotide may thus be a biologically inactive nucleotide. A biologically inactivated nucleotide may have a removable moiety protecting a group of the nucleotide, such as the 3' carbon oxygen or the terminal phosphate oxygen. A biologically inactive nucleotide may be a caged nucleotide or a blocked nucleotide. Suitable moieties include but are not limited to photoactivatable (caging) group, including a-carboxy-2-nitrobenzyl (CNB), 1-(2-nitrophenyl)ethyl (NPE), 4,5-dimethoxy-2-nitrobenzyl (DMNB), 1-(4,5-dimethoxy-2-nitrophenyl)ethyl (DMNPE) and 5-carboxymethoxy-2-nitrobenzyl (CMNB) (Molecular Probes). These groups are generally attached via terminal phosphate oxygen. The moiety may be removed by any suitable means. For example if the moiety is photolabile, flash photolysis of the moiety by ultraviolet light leads to a rapid and highly localized release of the biologically active nucleotide at the site of illumination. The moiety may be heat labile, and thus the biologically active nucleotide may be released by heat. If heat is used to biologically activate the nucleotide, the temperature requirements of the polymerase must be considered, and this is within the remit of the skilled person. For example the terminal phosphate may be esterified with a caging or blocking moiety.

The nucleotides may provided in a mixture of one or more suitable bases, preferably, one or more of adenine (A), guanine (G), thymine (T), cytosine (C). Two, three or preferably all four nucleotides (A, G, T, and C) are used in the process to synthesise DNA.

The nucleotides may all be natural nucleotides (i.e. unmodified), they may be modified nucleotides that act like natural nucleotides and are biologically active (i.e. LNA nucleotides—locked nucleic acid), they may be modified and biologically inactive or they may be a mixture of unmodified and modified nucleotides, and/or a mixture of biologically active and biologically inactive nucleotides. Each type (i.e. base) of nucleotide may be provided in one or more forms, i.e. unmodified and modified, or biologically active and biologically inactive.

In one aspect of the invention, the nucleotides are included in the reaction mixture and the supply of further nucleotides to the reaction mixture is controlled. According to this aspect, the nucleotides may be present in the reaction mixture at a starting concentration of less than 8 mM, less than 7 mM, less than 6 mM, less than 5 mM, less than 4 mM, less than 3 mM, less than 2 mM or less than 1 mM. The nucleotides are thus added to form the reaction mixture such that the starting concentration of nucleotides in the reaction mixture is 8 mM or less, preferably 5 mM or less, more preferably 4 mM or less. The starting concentration refers to the total concentration of nucleotides (all bases) in the reaction mixture at the start of the reaction.

The nucleotides may be present in the reaction mixture in a starting concentration sufficient to synthesise at least 0.3 g/l of DNA. It is preferred that the starting concentration is sufficient to synthesise 0.5 g/l DNA, more preferably 0.6 g/l or 0.65 g/l DNA. The volume given is the volume of the reaction mixture. The starting concentration of nucleotides will not be sufficient to synthesise the desired quantity of DNA from the reaction mix, i.e. it may not be sufficient to achieve the final yield. The starting concentration of nucleotides may be determined on the basis of the one or more polymerases in the reaction mixture.

Alternatively or additionally, the starting concentration of nucleotides may be defined as a ratio between the concentration of the polymerase and the concentration of the nucleotides. The ratio between the number of nucleotide molecules to each polymerase enzyme at the start may be up to 500,000:1, up to 300,000:1 or up to 200,000:1 or within 5,000:1 to 100,000:1, preferably 20,000:1 to 90,000:1, more preferably 30,000:1 to 80,000:1, more preferably 40,000:1 to 60,000:1. The ratio between the number of nucleotide molecules to each polymerase is preferably higher than 5,000:1. In a preferred aspect, the ratio of nucleotides: polymerase enzyme at the start is 50,000:1.

The reaction mixture is incubated under conditions promoting amplification of said template. Strand displacement amplification is preferred. Preferably, the conditions promote amplification of said template by displacement of replicated strands through strand displacement replication of another strand. The conditions comprise use of any temperature allowing for amplification of DNA, commonly in the range of 20 to 90 degrees centigrade. A preferred temperature range may be about 20 to about 40 or about 25 to about 35 degrees centigrade. A preferred temperature for LAMP amplification is about 50 to about 70 degrees centigrade.

Typically, an appropriate temperature is selected based on the temperature at which a specific polymerase has optimal activity. This information is commonly available and forms part of the general knowledge of the skilled person. For example, where phi29 DNA polymerase is used, a suitable temperature range would be about 25 to about 35 degrees centigrade, preferably about 30 degrees centigrade. The skilled person would routinely be able to identify a suitable temperature for efficient amplification according to the process of the invention. For example, the process could be carried out at a range of temperatures, and yields of amplified DNA could be monitored to identify an optimal temperature range for a given polymerase. The amplification may be carried out at a constant temperature, and it is preferred that the process is isothermal. Since strand displacement amplification is preferred there is no requirement to alter the temperature to separate DNA strands. Thus, the process may be an isothermal process.

Other conditions promoting amplification of the DNA template comprise the presence of suitable buffering agents/pH and other factors which are required for enzyme performance or stability. Suitable conditions include any conditions used to provide for activity of polymerase enzymes known in the art.

For example, the pH of the reaction mixture may be within the range of 3 to 10, preferably 5 to 8 or about 7, such as about 7.5. pH may be maintained in this range by use of one or more buffering agents. Such buffers include, but are not restricted to, MES, Bis-Tris, ADA, ACES, PIPES, MOBS, MOPS, MOPSO, Bis-Tris Propane, BES, TES, HEPES, DIPSO, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, CABS, phosphate, citric acid-sodium hydrogen phosphate, citric acid-sodium citrate, sodium acetate-acetic acid, imidazole and sodium carbonate-sodium bicarbonate.

While the application of heat (exposure to 95° Centigrade for several minutes) is used to denature double stranded DNA other approaches may be used which are more suitable for DNA synthesis. Double stranded DNA can be readily denatured by exposure to a high or low pH environment or where cations are absent or present in very low concentrations, such as in deionised water. The polymerase requires the binding of a short oligonucleotide primer sequence to a single stranded region of the DNA template to initiate its replication. The stability of this interaction and therefore the efficiency of DNA amplification may particularly be influenced by the concentration of metal cations and particularly divalent cations such as $Mg^{2+}$ ions which may be seen as an integral part of the process.

The reaction mixture may also comprise metal ions. The reaction mixture may also comprise salts of metals such as, but not limited to, salts of divalent metal ions: magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), or salts of monovalent metal ions, including but not limited to lithium ($Li^+$), sodium ($Na^+$) or potassium ($K^+$). The salts may include chlorides, acetates and sulphates. Other salts that may be included are ammonium salts, in particular ammonium sulphate. The skilled person would be aware that the supply of nucleotides in the form of a metal ion salt will affect the concentration of metal ions in the reaction mixture, and can take account of this additional source of metal ions if required. The total concentration of metal ions in the reaction mixture preferably includes all sources of metal ions.

Detergents may also be included in the reaction mixture. Examples of suitable detergents include Triton X-100, Tween 20 and derivatives of either thereof. Stabilising agents may also be included in the reaction mixture. Any suitable stabilising agent may be used, in particular, bovine serum albumin (BSA) and other stabilising proteins. Reaction conditions may also be improved by adding agents that relax DNA and make template denaturation easier. Such agents include, for example, dimethyl sulphoxide (DMSO), formamide, glycerol and betaine. DNA condensing agents may also be included in the reaction mixture. Such agents include, for example, polyethylene glycol or cationic lipid or cationic polymers.

It should be understood that the skilled person is able to modify and optimise amplification and incubation conditions for the process of the invention using these additional components and conditions on the basis of their general knowledge. Likewise the specific concentrations of particular agents may be selected on the basis of previous examples in the art and further optimised on the basis of general knowledge. As an example, the amount of polymerase present in the reaction mixture may be optimised. This may involve making further addition of polymerase enzyme to the reaction mixture during the DNA synthesis. As a further example, the amount of DNA template may be optimised. This may involve making further addition of DNA template to the reaction mixture during DNA synthesis. Further supply of polymerase enzyme and/or DNA template may be continuous or discontinuous, preferably discontinuous.

As an example, a suitable reaction buffer used in RCA-based methods in the art is 50 mM Tris HCl, pH 7.5, 10 mM $MgCl_2$, 20 mM $(NH_4)_2SO_4$, 5% glycerol, 0.2 mM BSA, 1 mM dNTPs. A preferred reaction buffer used in the RCA amplification of the invention is 30 mM Tris-HCl pH 7.4, 30 mM KCl, 7.5 mM $MgCl_2$, 10 mM $(NH_4)_2SO_4$, 4 mM DTT, 2 mM dNTPs. This buffer is particularly suitable for use with Phi29 RCA polymerase.

The reaction mixture may also comprise use of one or more additional proteins. The DNA template may be amplified in the presence of at least one pyrophosphatase, such as Yeast Inorganic pyrophosphatase. Two, three, four, five or more different pyrophosphatases may be used. These enzymes are able to degrade pyrophosphate generated by the polymerase from dNTPs during strand replication. Build-up of pyrophosphate in the reaction can cause inhibition of DNA polymerases and reduce speed and efficiency of DNA amplification. Pyrophosphatases can break down pyrophosphate into non-inhibitory phosphate. An example of a suitable pyrophosphatase for use in the process of the present invention is *Saccharomyces cerevisiae* pyrophosphatase, available commercially from New England Biolabs, Inc.

Any single-stranded binding protein (SSBP) may be used in the process of the invention, to stabilise single-stranded DNA. SSBPs are essential components of living cells and participate in all processes that involve ssDNA, such as DNA replication, repair and recombination. In these processes, SSBPs bind to transiently formed ssDNA and may help stabilise ssDNA structure. An example of a suitable SSBP for use in the process of the present invention is T4 gene 32 protein, available commercially from New England Biolabs, Inc.

The reaction mixture may be incubated under conditions promoting amplification of the DNA template, as described above. The amplification is preferably strand displacement replication. The reaction mixture comprises nucleotides, preferably at the starting concentration or starting ratio (to polymerase) discussed previously. The reaction mixture may further comprise metal ions.

In order to synthesise DNA, a supply of further nucleotides is required according to one aspect of the invention. The supply of nucleotides to the reaction mixture is controlled according to the first aspect of the invention. Thus, all of the nucleotides required for the synthesis of DNA are not added to the reaction mixture at the start of the process. The further nucleotides may be supplied or provided at any suitable time to the reaction mixture. The timing of the supply of further nucleotides to the reaction mixture and/or the amount of nucleotides supplied to the reaction mixture is controlled or directed. Thus, the reaction itself may be controlled by the precise supply of nucleotides. This control may be based upon theoretical calculations of the enzyme kinetics, or the control may be based upon measurable parameters of the reaction mixture, such that further nucleotides are supplied as they are required by the polymerase.

The further nucleotides may be supplied once the reaction mixture has been formed and incubated under conditions promoting amplification of the DNA template. The further nucleotides may be supplied after the amplification has started or been initiated. In one embodiment, the further supply of nucleotides commences at least 20 minutes, or at least 30 minutes or at least 40 minutes after the starting nucleotides is provided. However, supply can be initiated at the start of the reaction, particularly if the supply of nucleotides is continuous.

In one embodiment, the concentration or amount of nucleotides in the reaction mixture does not exceed a higher threshold during the process. The supply of nucleotides is controlled such that the concentration or amount of nucleotides does not exceed the higher threshold. The higher threshold may be 8 mM, or 7 mM or 6 mM or 5 mM or 4 mM or 3 mM or 2 mM nucleotides in the reaction mixture. Preferably the higher threshold is about 4 mM nucleotides in the reaction mixture. Similarly, in one embodiment, the concentration or amount of nucleotides in the relation mixture may not fall below a lower threshold during the process. The supply of nucleotides is controlled such that the concentration or amount of nucleotides does not fall below the lower threshold. This lower threshold may be 0.1 μM, 0.5 μM, 1 μM, 5 μM or 10 μM nucleotides in the reaction mixture. It is preferred that the concentration of nucleotides in the reaction mixture is maintained between the higher and the lower thresholds during the process. Thus, the concentration of nucleotides in the reaction mixture may be maintained between 0.0001 mM and 8 mM, preferably between 0.001 mM and 6 mM, most preferably between 0.01 mM and 5 mM. The concentration of nucleotides may be maintained by controlling the supply of the further nucleotides to the reaction mixture. In one embodiment, the concentration of nucleotides in the reaction mixture may be estimated by ion chromatography. Alternatively, the approximate concentration of nucleotides can be calculated by estimating the amount of DNA synthesised, as discussed herein.

Alternatively, the higher and lower thresholds may be described in relation to the ratio between the amount of nucleotides and polymerase present in the reaction mixture. The higher threshold may thus be 500,000:1 (nucleotides:polymerase), 200,000:1, 150,000:1, 100,000:1 or 80,000:1. The lower threshold may be 1,000:1, 1,500:1 or 2,000:1. Thus, the ratio of nucleotides to polymerase may be maintained at between 1,000:1 and 500,000:1, preferably 2,000:1 to 450,000:1, more preferably 5,000:1 to 400,000:1, most preferably between 10,000:1 and 100,000:1. Most preferably, the ratio is maintained at between 40,000:1 and 70,000:1, at about 50,000:1.

In one embodiment, the further nucleotides are supplied to the reaction mixture in one or more discrete additions, i.e. as aliquots. Any number of additions or aliquots are within the scope of this embodiment. Thus, 1, 2, 3, 4, 5, 6, 7, 8, 9, 10, 11, 12, 13, 14, 15, 16, 17, 18, 19, 20 or more, i.e. 20-25, 25-30, 35-40 additions or aliquots may be added to the reaction mixture. Thus, 1-50, 1-40, 1-30 or 1-20 aliquots may be used to supply the nucleotides. An aliquot may be a portion of the total amount of nucleotides required for or added to the process. The volume and/or concentration of nucleotides in the aliquot can vary depending on the requirements of the process. An aliquot may comprise a small amount of nucleotides, i.e. an amount sufficient to ensure that a particular concentration or amount of nucleotides is present in the reaction mixture. The nucleotides may be supplied to the reaction mixture as aliquots at regular intervals (i.e. every 30 minutes, every 60 minutes, every 90 minutes, every 120 minutes, every 180 minutes or every 240 minutes or any other suitable time period). The nucleotides may be supplied to the reaction mixture as aliquots at irregular intervals. For example, the time period between each supply of nucleotides can be shorter initially, and then increase as the process proceeds, or vice versa. The aliquots may be provided to maintain a constant concentration of nucleotides in the reaction mixture, or may be provided to replenish the concentration of nucleotides to the starting concentration. In a preferred embodiment, the nucleotides are supplied such that the concentration in the reaction mixture does not exceed 8 mM, or 7 mM or 6 mM or 5 mM or 4 mM. In a preferred embodiment, the nucleotides are supplied in such a way to ensure that the concentration or amount of nucleotides in the reaction mixture falls within the higher and lower threshold.

It is preferred that the aliquot is not supplied solely to replace a volume of reaction mixture taken for analysis or testing, but is supplied because the reaction requires further nucleotides. It is preferred that the testing of the reaction mixture is non-invasive and that no material is withdrawn from the reaction mixture until the reaction is complete.

Further nucleotides may be supplied in response to a need for more nucleotides in the reaction mixture. This can be determined by several parameters, including, but not limited to the rate of DNA synthesis, the concentration of DNA synthesised or the viscosity or volume of the reaction mixture. The rate of DNA synthesis can be calculated from the concentration of DNA synthesised over time. As the rate of DNA synthesis starts to decrease, further nucleotides may be supplied. Alternatively, the concentration of DNA synthesised can be monitored, by methods discussed further below. As the concentration of DNA increases to a threshold level, further nucleotides may be supplied. The viscosity of the reaction mixture may be measured, and an increase in viscosity may indicate the requirement for further nucleotides. The viscosity of the reaction may be measured with a viscometer.

In one embodiment, the further nucleotides are supplied to the reaction mixture continuously, i.e. they are added in a continuous manner to the reaction mixture. Alternatively put, the nucleotides may be a drip-fed or constantly supplied. The supply of further nucleotides according to this embodiment may be in sufficiently small amounts such that the supply of nucleotides matches the demand by the polymerase for further nucleotides. In this embodiment, the constant supply of nucleotides maintains an about constant concentration of nucleotides in the reaction mixture. It is preferred that the constant supply of further nucleotides to the reaction mixture ensures that the concentration of nucleotides in the reaction mixture is maintained within the higher and lower thresholds.

The further nucleotides may be physically provided to the reaction mixture, i.e. they are external to the reaction mixture. Thus, the supply may originate from an external source, such as a reservoir. This reservoir may be connected to the reaction mixture. The nucleotides may be pumped into the reaction mixture. Thus, the nucleotides and the reaction mixture are physically separate and the supply of the further nucleotides is a physical supply of nucleotides. Alternatively, the nucleotides may be supplied via an osmotic pump. An osmotic pump provides a method for controlled and continuous nucleotide supply.

The nucleotides may alternatively be provided to the reaction mixture by activating biologically inactivated nucleotides, such as those discussed previously. In order to supply the nucleotides to the reaction mixture, the biologically inactive nucleotides are activated by suitable means. Thus, the further nucleotides may comprise any suitable biologically inactive nucleotides. The biologically inactive nucleotides may be included in the reaction mixture at the start but only supplied to the reaction mixture by controlled activation. Alternatively, the biologically inactive nucleotides can be physically added to the reaction mixture in aliquots or continuously, and subsequently activated to supply the nucleotides to the reaction mixture. The activation may be physical (i.e. heat or light) or chemical, and it is the control of activation that controls supply of the nucleotide.

The supply of nucleotides to the reaction mixture may be controlled until the synthesis of DNA is complete, for example once the DNA template is exhausted and no further incorporation is possible. Alternatively, the reaction may be complete once the expected or desired yield of DNA has been synthesised. Such a yield may be based upon the amount of nucleotides added. The synthesis of DNA may be complete once the required amount of DNA has been synthesised, such as 1 g per litre of reaction mixture 2 g/l, 3 g/l, 4 g/l, 5 g/l or up to or exceeding 10 g/l. The synthesis of DNA may be complete once the rate of DNA synthesis has decreased and further supply of nucleotide does not increase this rate, the reaction mixture runs out of another component (such as, but not limited to the primer), the polymerase enzyme is inactivated, the inorganic pyrophosphatase is inactivated, no further single stranded template is available, required co-factors such as metal cations are exhausted, the viscosity of the reaction mixture reaches a certain threshold, the volume of the reaction mixture reaches a certain threshold or the polymerase is inhibited.

The yield of the reaction relates to the amount of DNA synthesised. The expected yield from a process according to the present invention may exceed 10 gram/litre of reaction mixture, or 10, 9, 8, 7, 6, 5 4, 3, 2 or 1 g/l. The present invention improves the yield possible from enzymatic synthesis of DNA. It is an object of the present invention to improve the yield of a cell-free enzymatic DNA synthesis process, such that DNA can be synthesised on a large scale in a cost-effective way. The present invention allows the manufacture/synthesis of DNA economically on an industrial scale using an enzymatic process catalysed by a polymerase. The present process allows the efficient incorporation of nucleotides into the DNA product. It is thought that the process of the invention will allow reaction mixtures to be scaled up into several litres, including tens of litres. The improved yield, rate of DNA synthesis, productivity or processivity may be compared to an identical reaction mixture where all of the nucleotides are supplied at the start. It is thought that the yield may be improved by controlling the supply of further nucleotides to the reaction mixture, as demonstrated in the Examples.

The rate of DNA synthesis relates to the amount or concentration of DNA synthesised per minute of the process. In the Examples, it will be seen that the rate of DNA synthesis progressively slows as the process progresses.

The productivity of the process, or the rate of DNA output per unit of nucleotide supplied, may be increased by using the process or processes of the invention.

In one embodiment, the present invention relates to a process for enhancing the synthesis of DNA. This enhancement may be compared to an identical reaction mixture, with the exception that all of the required components, including the nucleotides are added at the start. No further additions are made to this control reaction mixture.

In one aspect, there is provided a cell-free process for synthesising DNA comprising contacting a DNA template with at least one polymerase in the presence of one or more primers, nucleotides and metal cations to form a reaction mixture, under conditions promoting amplification of said template by displacement of replicated strands through strand-displacement replication of another strand, wherein further metal cations are supplied in a controlled manner to the reaction mixture.

Alternatively put, the amplification occurs by strand displacement replication of the template. The invention thus provides a cell-free process for synthesising DNA comprising contacting a DNA template with at least one polymerase in the presence of one or more primers, nucleotides and metal cations to form a reaction mixture, under conditions promoting strand displacement replication of said template, wherein further nucleotides and further metal cations are supplied in a controlled manner to the reaction mixture.

It is preferred that the rate of reaction of the cell-free process for synthesising DNA is controlled by supplying further cations in a controlled manner to the reaction mixture.

The supply of metal cations to the reaction mixture may be controlled according to this aspect of the invention. Such control is thought to improve the rate of DNA synthesis, particularly in a large-scale process. One or more metal cations may be present in the reaction mixture at the start. Thus, the reaction mixture may also comprise one or more metal cations, preferably supplied as salts. The supply of further metal cations to the reaction mixture may be controlled. One or more metal cations may be supplied. Suitable metal cations include divalent metal ions: magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), or monovalent metal ions, including but not limited to lithium ($Li^+$), sodium ($Na^+$) or potassium ($K^+$). The metal cations are preferably supplied as salts. The salts may include chlorides, acetates and sulphates, and it is preferred that the metal cations are supplied as chloride salts. Other salts that may be included are ammonium salts, in particular ammonium sulphate. It is preferred that the metal cations are magnesium or manganese, most preferably magnesium. In a most preferred embodiment, the metal cations are provided as magnesium chloride.

In order to synthesise DNA, a supply of further metal cations is required according to one aspect of the invention. The supply of metal cations to the reaction mixture is controlled according to the second aspect of the invention. Thus, all of the metal cations required for the synthesis of DNA are not added to the reaction mixture at the start of the process. The further metal cations may be supplied or provided at any suitable time to the reaction mixture. The timing of the supply of further metal cations to the reaction mixture and/or the amount of metal ions supplied to the reaction mixture is controlled or directed. Thus, the reaction itself may be controlled by the precise supply of metal ions. This control may be based upon theoretical calculations of the enzyme kinetics, or the control may be based upon measurable parameters of the reaction mixture, such that further metal ions are supplied as they are required. The supply of further metal cations may be controlled in parallel or in conjunction with the controlled supply of further nucleotides. The supply may be independently controlled or controlled together.

The further metal cations may be supplied once the reaction mixture has been formed and incubated under conditions promoting amplification of the DNA template. The further metal cations may be supplied after the amplification has started or been initiated. In one embodiment, the further supply of metal cations commences at least 20 minutes, or at least 30 minutes or at least 40 minutes after the starting concentration of metal cations is provided. However, supply can be initiated at the start of the reaction, particularly if the supply of metal cations is continuous.

In one embodiment, the concentration or amount of free or unbound metal cations in the reaction mixture does not exceed a higher threshold during the process. The supply of metal cations is controlled such that the concentration or amount of free or unbound metal cations does not exceed the highest threshold. The highest threshold may be 4 mM, 3 mM or 2 mM in the reaction mixture. Preferably the highest threshold is about 3 mM in the reaction mixture. Similarly, in one embodiment, the concentration or amount of free metal cations in the reaction mixture may not fall below a lowest threshold during the process. The supply of metal cations is controlled such that the concentration or amount of free metal cations does not fall below the lowest threshold. This lowest threshold may be 0.03 µM, 0.15 µM, 0.3 µM, 1.5 µM, or 3 µM in the reaction mixture. It is preferred that the concentration of free metal cations in the reaction mixture is maintained between the highest and the lowest thresholds during the process. Thus, the concentration of free metal cations in the reaction mixture may be maintained between 0.03 µM and 4 mM, or 0.5 µM to 3 mM or 1 µM to 2 mM or 10 µM to 1 mM. Preferably, the concentration of free metal cations in the reaction mixture is maintained between 1 mM and 1.5 mM.

Alternatively, the highest threshold may be 10 mM, 8 mM, 6 mM, 4 mM, 3 mM or 2 mM in the reaction mixture. Preferably the highest threshold is about 3 mM in the reaction mixture. Similarly, in one embodiment, the concentration or amount of free metal cations in the reaction mixture may not fall below a lowest threshold during the process. The supply of metal cations is controlled such that the concentration or amount of free metal cations does not fall below the lowest threshold. This lowest threshold may be 0.03 µM, 0.15 µM, 0.3 µM, 1.5 µM, 3 µM and 5 µM in the reaction mixture. It is preferred that the concentration of free metal cations in the reaction mixture is maintained between the highest and the lowest thresholds during the process. Thus, the concentration of free metal cations in the reaction mixture may be maintained between 0.03 µM and 10 mM, or 0.15 µM to 8 mM or 0.3 µM to 6 mM or 1.5 µM to 3 mM. Preferably, the concentration of free metal cations in the reaction mixture is maintained between 0.15 µM and 5 µM.

The concentration of free metal cations may be maintained by controlling the supply of the further metal ions to the reaction mixture. In one embodiment, the concentration of free metal ions in the reaction mixture may be estimated by, atomic absorption spectroscopy, ion chromatography and other methods known in the art. Alternatively, the approximate concentration of free metal cations can be calculated by estimating the amount of DNA synthesised, as discussed herein. For the avoidance of doubt, metal cations, such as magnesium ions, can be bound to different entities in the reaction mixture including, but not limited to pyrophosphate, phosphate and DNA. These ions are bound and are not free.

In one embodiment, the further metal cations are supplied to the reaction mixture in one or more discrete additions, i.e. as aliquots. Any number of additions or aliquots are within the scope of this embodiment. Thus, 1, 2, 3, 4, 5, 6, 7, 8, 9, 10, 11, 12, 13, 14, 15, 16, 17, 18, 19, 20 or more, i.e. 20-25, 25-30, 35-40 additions or aliquots may be added to the reaction mixture. Thus, 1-50, 1-40, 1-30 or 1-20 aliquots may be used to supply the metal cations. An aliquot may be a portion of the total amount of metal cations required for or added to the process. The volume and/or concentration of metal cations in the aliquot can vary depending on the requirements of the process. An aliquot may comprise a small amount of metal cations, i.e. an amount sufficient to ensure that a particular concentration or amount of metal cations is present in the reaction mixture. The metal cations may be supplied to the reaction mixture as aliquots at regular intervals (i.e. every 30 minutes, every 60 minutes, every 90 minutes, every 120 minutes, every 180 minutes or every 240 minutes or any other suitable time period). The metal cations may be supplied to the reaction mixture as aliquots at irregular intervals. For example, the time period between each supply of metal cations can be shorter initially, and then increase as the process proceeds, or vice versa. The aliquots may be provided to maintain a constant concentration of metal cations in the reaction mixture, or may be provided to replenish the concentration of metal cations to the starting concentration, preferably the optimal free metal ion concentration.

In a preferred embodiment, the metal cations are supplied in such a way to ensure that the concentration or amount of free metal cations in the reaction mixture falls within the highest and lowest threshold.

Further metal cations may be supplied in response to a need for such in the reaction mixture. This can be determined by several parameters, as discussed previously.

In one embodiment, the further metal cations are supplied to the reaction mixture continuously.

The further metal cations may be physically provided to the reaction mixture, i.e. they are external to the reaction mixture.

It is preferred that the supply of further nucleotides is also controlled.

In a further aspect, there is provided a cell-free process for synthesising DNA comprising contacting a DNA template with at least one polymerase in the presence of one or more primers, nucleotides and metal cations to form a reaction mixture, under conditions promoting amplification of said template by displacement of replicated strands through strand-displacement replication of another strand, wherein further nucleotides and metal cations are supplied in a controlled manner to the reaction mixture.

There is also provided a cell-free process for synthesising DNA comprising contacting a DNA template with at least one polymerase in the presence of nucleotides and metal cations to form a reaction mixture, under conditions promoting strand displacement amplification of said template, wherein further nucleotides and further metal cations are supplied in a controlled manner to the reaction mixture.

The further nucleotides and further metal ions may be supplied together or separately. The controlled supply of the further nucleotides or further metal cations may be achieved as discussed previously in relation to these entities.

The supply of the metal cations or further metal cations may be in parallel to the supply of nucleotides, or may be at different times to the supply of nucleotides.

It is preferred that the further metal cations may be supplied to the reaction mixture with the supply of the nucleotides, particularly where the metal cations are monovalent. The metal cations and the nucleotides may thus be supplied as a mixture. The supply of metal cations and nucleotides may thus be combined, although it is preferred that they are kept separate.

The supply of further metal cations and/or further nucleotides may be as described for each of these entities individually.

In a preferred embodiment of the invention, the metal cations and nucleotides are supplied such that a ratio (amount) of metal cations:nucleotides is between 9:1 and 1:9, or 6:1 and 1:6 or 3:1 or 1:3, or 1:1. Preferably the ratio between the amounts of these in the reaction mixture is between about 3:1 and 1:3, preferably about 3:1. These ratios are particularly preferred where the metal cation is a divalent metal cation, such as, but not limited to magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$).

It is thought that maintaining the ratio of metal cations:nucleotides, preferably magnesium cations, may be important in controlling the rate of DNA synthesis. The ratio of nucleotide:polymerase may also be maintained as discussed previously. Thus, controlling these two ratios, by controlling the supply of the nucleotides and metal cations, may control the synthesis of DNA.

With relevance to any aspect of the invention, if the nucleotides are supplied as salts of metal cations, the concentration of metal cations in these salts supplied to the reaction mixture will include these metal cations. The skilled person would be aware that supplying nucleotides in the form of a metal cation salt will affect the concentration of metal cations in the reaction mixture, and can take account of this additional amount.

Nucleoside triphosphates (ATP, GTP, CTP and TTP) by virtue of their chemical properties have the potential to interfere with DNA amplification in a number of ways if high concentrations are used in order to increase DNA product yields. High concentrations may be considered to be concentrations of dNTPs higher than 4 mM in the reaction mixture. The phosphate groups of dNTPs are able to interact with mono and divalent metal cations and possess the strongest affinity for $Mg^{2+}$. For example, the affinity of ATP for $Mg^{2+}$ is over 700 times greater than $Na^+$ and nearly 400 times greater than $Li^+$.

During amplification, polymerases release pyrophosphate from nucleotides that are incorporated into the growing DNA chain. Pyrophosphate has a binding affinity for $Mg^{2+}$ ions similar to ATP and so free $Mg^{2+}$ ions are not released by this process. The consequence of using high starting concentrations of nucleotides during amplification will be to reduce the levels of free $Mg^{2+}$ ions. Since $Mg^{2+}$ ions may be required for polymerase catalytic activity, suboptimal levels caused by interaction with phosphates or phosphate groups is likely to be detrimental to efficient amplification. However, conversely, high concentrations of $Mg^{2+}$ ions have been shown to affect the fidelity of some DNA polymerases. Reaction concentrations of $Mg^{2+}$ ions may therefore be thought to be critical for DNA yield and quality.

Pyrophosphate breakdown may be catalysed by an enzyme and might be expected to release bound $Mg^{2+}$ ions from the pyrophosphate. However, $Mg^{2+}$ ions bind $PO_4^{3-}$ ions to form essentially insoluble $Mg_3(PO_4)^2$ (solubility of 0.01 mM in water at 20° C.).

$Mg^{2+}$ ions will also bind to synthesised DNA.

The level of free $Mg^{2+}$ ions in any DNA polymerase catalysed reaction at any particular point in time will be dependent on the starting concentration, the total concentration of molecules capable of binding the cation and pH of the reaction. Since the processes are in equilibrium there is always likely to be some free $Mg^{2+}$. In one embodiment, the level of free $Mg^{2+}$ is controlled by controlling the supply of free $Mg^{2+}$ ions, preferably as magnesium salts, to the reaction mixture.

Polymerases that are able to amplify circular DNA templates through a rolling circle, strand displacement mechanism and are capable of producing long linear concatameric repeats of the template. Such rolling circle strand displacing polymerases are preferred. It is reported, for example, Phi29 DNA polymerase can amplify circular DNA templates to produce linear repeats of up to 77 kilobases in length. These very long molecules behave like polymers and can significantly alter the rheological properties of the reaction by increasing the viscosity. This increase in viscosity can be measured by changes in pressure which can be directly correlated to the concentration of synthesised DNA. Such measurements can be made continuously or at set times to provide a signal, preferably an on-line signal that may be used to indicate the status of the reaction. The supply of further nucleotides may be controlled in response to the pressure signal. Such a supply of nucleotides, in response to a signal indicating a parameter of the reaction mixture, may be made in order to increase the yield and/or productivity of the reaction mixture.

Pressure differential measurements to estimate DNA concentrations have an important advantage over assays based on the binding of fluorescent chemical reagents such as Syto dyes. Unlike these reagents which only bind to double stranded DNA, pressure differential measurements do not give erroneous estimates of DNA in samples containing single stranded forms.

In one embodiment, the supply of nucleotides is controlled in response to a signal. The signal may be any suitable signal and may be an on-line signal. It is preferred that the signal relates to the concentration of DNA, particularly is based upon an estimate of the total concentration of DNA in the reaction mixture. The signal may alternatively relate to the volume of the reaction mixture. The supply of further metal ions may be similarly controlled in response to a signal. The signal may be the same or different.

A preferred signal is one which relates to the viscosity of the reaction mixture. The viscosity of the reaction mixture may provide an estimate of the concentration of DNA in the reaction mixture. The viscosity may be measured by any suitable means, including a viscometer. It is preferred that the viscosity is measured by changes in pressure. The pressure differential may be measured by a pressure sensor, pressure transducers, pressure transmitters, pressure indicators, piezometers or manometers. In one embodiment, the pressure differential may be created using a reciprocating pump that removes and replaces a portion of the reaction mixture. It is preferred that the reaction is monitored in real-time in a non-invasive fashion such as indicated here.

The process of the invention may be performed as a batch reaction. In this embodiment, the reaction mixture is present in a reactor. The supply of further nucleotides and/or further metal cations may be fed into the reactor. Thus, the process may be performed in a fed-batch reactor. Alternatively, the process may be performed in a continuous flow reactor. Such reactors are within the knowledge of the skilled person. A particularly preferred format is presented below.

In an embodiment, one or more processing enzymes are supplied to the reaction mixture in one or more discrete additions, i.e. as aliquots. Any number of additions or aliquots is within the scope of this embodiment. Thus, 1, 2, 3, 4, 5, 6, 7, 8, 9, 10, 11, 12, 13, 14, 15, 16, 17, 18, 19, 20 or more, i.e. 20-25, 25-30, 35-40 additions or aliquots may be added to the reaction mixture. Thus, 1-50, 1-40, 1-30 or 1-20 aliquots may be used to supply the processing enzymes. An aliquot may be a portion of the total amount of processing enzyme required for or added to the process. The volume and/or concentration of processing enzyme in the aliquot can vary depending on the requirements of the process. An aliquot may comprise a small amount of processing enzyme, i.e. an amount sufficient to ensure that a particular concentration or amount of processing enzyme is present in the reaction mixture. The processing enzyme may be supplied to the reaction mixture as aliquots at regular intervals (i.e. every 30 minutes, every 60 minutes, every 90 minutes, every 120 minutes, every 180 minutes or every 240 minutes or any other suitable time period). The processing enzyme may be supplied to the reaction mixture as aliquots at irregular intervals. For example, the time period between each supply of processing enzyme can be longer initially, and then decrease as the process proceeds, or vice versa.

Processing enzymes may be supplied in response to a need for such in the reaction mixture. This can be determined by several parameters, as discussed previously, including the concentration of DNA in the reaction mixture and/or the rate of DNA synthesis.

The processing enzymes may be physically provided to the reaction mixture, i.e. they are external to the reaction mixture. These enzymes may be held in a separate reservoir and be released in a controlled manner into the reaction mixture.

It is preferred that the processing enzyme has a single turnover, such as protelomerase, as then controlling the amount of processing enzyme directly controls the amount of DNA processed by the enzyme. The processing enzyme may be added together with the further nucleotides, or after the further nucleotides. Should further metal ions also be required, it may be preferred that these are added after the addition of the processing enzyme, such that the processing of the DNA occurs before further metal ion is added.

The process may be performed on any suitable apparatus. A particular apparatus suitable for carrying out the process will now be described. Synthesis apparatus 1 is constructed on a self-contained chassis 11 and provided with an openable front cover 12 to allow access to the main components. The front cover 12 is desirably made of a transparent material but may be tinted to protect the reaction components from excessive light levels. It also serves to limit ingress of contaminants. The apparatus is provided with externally accessible power switch and power input 13, e.g. on a side of the apparatus. In addition there are input/output ports 14 to allow the apparatus to communicate with and/or be controlled by a general purpose computer executing laboratory automation software such as, for example, Labview™ supplied by National Instruments Corporation of Texas, USA. An operation indicator light 15 is provided at a position to be visible from the front of the apparatus and indicates whether or not the apparatus is in operation.

The central component of the synthesis apparatus is a jacketed reaction vessel 2 which may have a volume greater than 30 ml, such as 50 ml, 75 or 120 ml. The volume of the reaction vessel may be less than 300 ml. The volume of the reaction vessel can be selected in accordance with the intended use of the apparatus and the amount of product that is intended to be made in a batch, or the rate of production in a continuous process. Clearly, the size of the reaction vessel sets an upper limit on the amount of product that can be produced in a batch The aspect ratio of the reaction vessel may be no greater than 8:1, or no greater than 7:1, 6:1 or 5:1. If the reaction vessel is too tall, it becomes harder to effect thorough mixing of the contents by withdrawal and return of reaction mixture. If the reaction vessel is too wide, it becomes more difficult to ensure an even temperature throughout, especially with smaller reaction volumes. Agitation of the mixture can assist in obtaining the desired temperature throughout the mixture, especially if the reaction mixture is heated to 95° C. Reaction vessels with aspect ratios within the above limits are adaptable to different quantities of reaction components.

Figure 3:
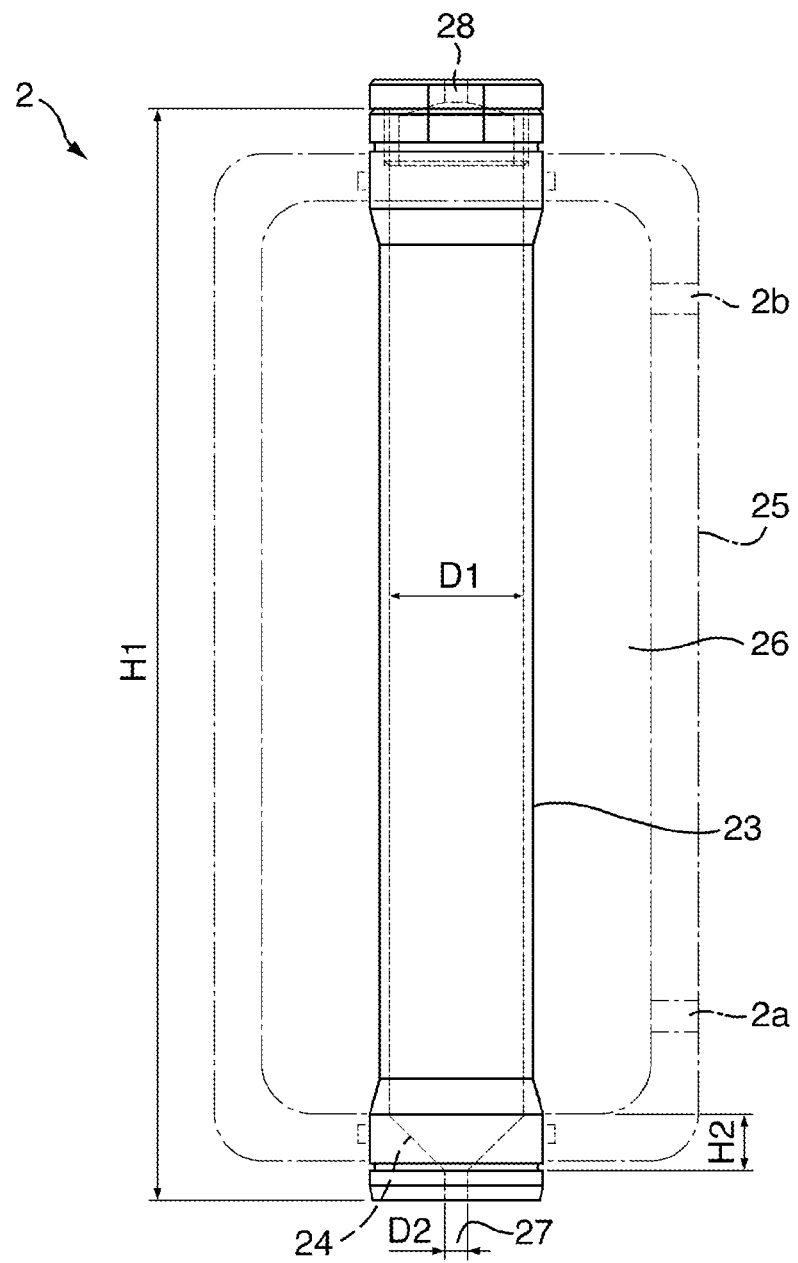
FIG. 3 is a cross-sectional view of a reaction vessel useful according to an embodiment of the invention.

A reaction vessel 2 which may be used in an embodiment of the invention is shown in cross-section in FIG. 3. The reaction vessel 2 comprises an inner vessel 23 surrounded by a jacket 25. Temperature control fluid is circulated though the space 26 between inner vessel 23 and jacket 25 in order to control the temperature of the contents of the inner vessel 23. Lower port 27 and upper port 28 are provided to connect the inner vessel to selection valves 32*b*, 32*a* respectively.

The inner vessel 23 may have a main part which has the form of a cylinder of diameter D1, e.g. in the range of 20 to 50 mm, preferably 25 to 35 mm, and a tapering part 24 connecting the cylindrical part to the lower port 27. The overall height H1 of the inner vessel may be in the range of from 150 mm to 300 mm, desirably 200 mm to 250 mm. The height of the tapering part 24 may be in the range of from 5 to 20 mm, preferably 10 to 15 mm. The angle of the side walls of the tapering part may be in the range of from 30 to 60° relative to the axis of the inner vessel, preferably about 45°. The diameter D2 of the lower port 27 may be in the range of from 5 to 10 mm.

The reaction vessel may have a non-constant cross-section, for example having a downwards taper throughout its height or a central bulge.

The temperature of the reaction vessel may be controlled by a flow of temperature control fluid through the outer jacket to the reaction vessel. The temperature control fluid may be supplied by inlet 2*a* and removed from outlet 2*b* by a recirculating temperature control device 22. The recirculating temperature control device controls the temperature of the temperature control fluid by heating and/or cooling the fluid. The reaction vessel may be maintained at a constant temperature, e.g. in spite of the occurrence of endothermic or exothermic reactions, or may be controlled to follow a desired temperature profile. The temperature control fluid may be water or oil. The temperature control fluid may be supplied via ports 16 provided on the chassis of the apparatus. A suitable recirculating temperature control device is the Presto A30 Temperature Control System manufactured by Julabo USA, Inc. of Pennsylvania, USA. In an embodiment of the invention, the recirculating temperature control device 22 comprises ohmic heaters and/or Peltier devices. In an embodiment, the temperature of the reaction vessel is controllable to a temperature with the range of from 4° C. to 95° C. with a precision of 0.01° C.

Temperature-controlled reservoirs 4a-4c may be provided for reaction components to be used in the synthesis reaction. The reaction components are held in syringes 42a-42c, e.g. disposable polypropylene syringes, which are mounted in temperature control devices 41a-41c. The temperature control devices in this embodiment comprise blocks of conductive material, e.g. aluminium, having bores to closely receive the syringes 42a-42c. A thermally conductive paste can be provided if desired to increase thermal conductivity between the block and the syringes. Heating/cooling devices, e.g. ohmic heaters or Peltier devices, are attached to the thermally conductive blocks in order to control the temperature thereof and hence of the reaction components stored in the reservoirs 42a-42c.

Temperature control devices 41a-41c may be used either to heat or to cool the stored reaction components. Some reaction components are desirably held at a low temperature, e.g. about 4° C., in order to prevent degradation thereof. Primers can be stored at an elevated temperature so as to prevent and/or reduce primer diming. The reservoirs can also be heated to denature and anneal templates and primers prior to addition to the reaction vessel. As with the main temperature control of the reaction vessel, the temperature controlled reservoirs can be maintained at a constant temperature or follow a desired temperature profile, e.g. to heat a reaction component just before addition to the reaction vessel. In an embodiment the temperatures of the temperature-controlled reservoirs are independently controllable within a range of from 4° C. to 95° C. with a precision of 0.01° C.

One or more in-line heaters (not shown) may be provided to raise the temperature, e.g. to 95° C., of a reaction component such as a primer before addition to the reaction vessel. The/or a heater is provided on the conduit between a reservoir 4a-c, 5a-g and selection valve 32c and/or between selection valve 32a and reaction vessel 2.

In this incarnation, one of the temperature controlled reservoirs 4c comprises two reservoir syringes 42c and 42c' in thermal contact with a single temperature control block 41c. This is useful where two reaction components need to be maintained at the same temperature or where a larger volume of a single reaction component is required for a desired reaction.

The apparatus also comprises a plurality of further reservoirs 5a-5g that are not provided with temperature controlling devices. In this embodiment there are seven such reservoirs, in other embodiments more or fewer are provided. The further reservoirs 5a-5g can also comprise syringes, e.g. glass or polypropylene syringes, that can be removed and disposed of when empty. The use of syringes is advantageous as the volume of the reservoir automatically reduces as reaction components are withdrawn. A similar effect can be achieved with collapsible bags or tubes. If a rigid container is used, it is desirable that a filter is provided in any vent to atmosphere in order to prevent ingress of contaminants.

Conveniently, a rotary stand 51 is provided to mount reservoirs 5. If a reaction component is required in large quantities, the apparatus can be provided with ports to connect to an external reservoir. Desirably, the apparatus is laid out so as to minimise the lengths of conduit required to connect the reservoirs to the selection valves. The conduits may be detachable from the reservoirs and then can be attached to a manifold which is connected to a supply of cleaning fluid or water for rinsing. In this way the entire apparatus can be cleaned flushed in situ, i.e. without being dismantled.

Reservoirs 4a-c and 5a-g may have a capacity of from 3 to 10 ml, e.g. about 5 ml. One or more larger reservoirs can be provided, e.g. for buffer solutions, with a capacity of from 10 to 500 ml, e.g. about 250 ml.

Supply of a reaction component to the reaction vessel may be effected by a reciprocating syringe pump 3a. This pump is referred to as the supply pump. This comprises a syringe 31a, e.g. a glass or polypropylene syringe, driven by a solenoid 33a and connected to a controllable selection valve 32a to selectively connect the solenoid to each of the reservoirs and the reaction vessel. To add a controlled amount of a reaction component to the reaction vessel, the selection valve 32a is first used to connect the pump syringe to the relevant reservoir then the solenoid is actuated to draw into the syringe the relevant volume of the reaction component. Next, the selection valve 32a is used to connect the syringe 31a to the reaction vessel 2 and the solenoid reversed to drive the syringe contents out into the reaction vessel. With this arrangement, it is possible to quickly add quantities of desired reaction components sequentially to the reaction vessel without requiring multiple syringe pumps and multiple inlets to the reaction vessel. However, if it is desirable to add multiple reaction components simultaneously to the reaction vessel it is possible to provide multiple supply pumps 3a. This can also be desirable if it is necessary to keep certain reaction components absolutely separate prior to their addition to the reaction vessel.

Further, a second reciprocating syringe pump 3b may be used to agitate the contents of the reaction vessel as well as to remove reaction mixture or product either at the end of the reaction or for sampling purposes during a reaction process. This pump is referred to as the withdrawal pump and comprises a syringe 31b driven by a solenoid 33b. The second syringe pump 3b is connected to an outlet at the bottom of the reaction vessel via a second selection valve 32b. To agitate the contents of the reaction vessel, the second selection valve 32b is used to connect the syringe 31b to the reaction vessel whilst an amount of the reaction mixture is withdrawn from the reaction vessel and then returned thereto. The amount of the reaction mixture that is withdrawn and the rate at which it is returned can be controlled in order to control the degree of agitation that is effected. Such agitation can be effected continuously through the course of a reaction, periodically or at specific times relating to the addition of reaction components.

Alternatively or additionally, the second reciprocating syringe pump 3b may be also connected to reservoir 4a and can be used to supply the reaction component stored in that reservoir to the reaction vessel 2.

A pressure sensor 82 may be provided on a short spur connected to the conduit between reaction vessel 2 and selection valve 32b or between selection valve 32b and withdrawal pump 3b. During the withdrawal and return of material from or to the reaction vessel 2, the pressure measured by the sensor 82 is indicative of the viscosity of the mixture being transferred: the higher the pressure, the higher the viscosity. In particular, the amplitude of pressure variations during cyclic withdrawal and return of material is indicative of the viscosity of the reaction mixture. The exact relationship between pressure and viscosity is dependent on various factors including the rate of withdrawal or return of material, the diameter of the conduits used and the geometry of the reaction vessel. This relationship can be determined theoretically or by calibration. In an embodiment, the exact relationship is not necessary and the signals from pressure sensor 82 can simply be used to detect changes in the reaction mixture without knowing its exact viscosity. In a reaction where the viscosity increases due to product formation, the signal from the pressure sensor can be used to control the reaction. By activating the pump to deliver one or more appropriate reagents from one or more of the reservoirs at an appropriate rate or in an appropriate quantity based on the pressure signal, it is possible to increase product yield. In other cases, the pressure signal may indicate completion of the reaction or a stage in the reaction and so be used to trigger harvesting of the product or addition of components for a next stage.

A signal from the pressure sensor 82 may be used to control the rate of withdrawal and/or return of mixture to the reaction vessel to ensure that that DNA material in the mixture is not damaged by shear forces. The rate of withdrawal and/or return of mixture may be controlled to ensure that a pressure limit is not exceeded. The pressure limit can be viscosity dependent.

To remove material e.g. reaction product from the reaction vessel, the withdrawal pump 3b is first connected to the reaction vessel by the second selection valve 32b and the solenoid operated to withdraw the piston of the syringe so as to withdraw material from the reaction vessel 2. The withdrawal pump is then connected to an exit port 7 by the second selection pump and the solenoid 33b activated to eject the collected material through the exit port 7.

Exit port 7 can be connected to, for example, a container for reaction product, a sample container, a measurement device or any other apparatus. It is also possible for a sample that has been removed for measurement purposes to be returned to the reaction vessel after the measurement.

The withdrawal pump 3b may have a larger capacity than the supply pump 3a so that, for example, the entire reaction vessel can be emptied in a single pumping operation. Such a large capacity for the withdrawal pump 3b is also desirable to assist in cleaning the apparatus by flushing large volumes of cleaning solution and/or deionised water through the entire system. To this end, the apparatus can be provided with additional large reservoirs to hold sufficient quantities of cleaning solution and deionised water.

A single pump may be used to supply reaction components, to agitate the reaction mixture and to withdraw reaction mixture and/or product.

The supply pump 3a and/or withdrawal pump 3b may comprise another form of pump, e.g. a peristaltic pump.

The apparatus also comprises a waste vessel 6 which is connected to the atmosphere via a vent 62 which may be provided with a one-way valve. Waste vessel 6 is connected to the upper part of reaction vessel 2 so as to provide a vent therefore and prevent a build-up of pressure in reaction vessel 2. Conduits are also provided to connect waste vessel 6 with selection valves 32a and 32b so as to allow dumping of product from the reaction vessel and any unused and undesired reaction components. The waste vessel can also be used to receive cleaning and rinsing fluids during in-situ cleaning and rinsing as well as small amounts of reaction components from priming of the conduits to enable exact delivery of desired amounts to the reaction vessel.

Waste vessel 6 may be omitted. In this case it is desirable to provide a safety valve to reaction vessel 2 and to provide connections from selection valves 32a, 32b to an external drain.

Operation of the apparatus is controlled by a controller 8 which is electrically connected to the temperature control devices 41a-c, to selection syringes 32a-b, to solenoids 33a-b, to temperature control device 22 and to pressure sensor 82 so as to control those components of the apparatus. Controller 8 also comprises an interface 81 allowing connection to an external computer 9 for overall control of the process to be carried out.

The controller 8 may be pre-programmed to perform specific commonly used routines such as priming, sampling, harvesting, rinsing and cleaning. In an embodiment, controller 8 simply passes commands from the external computer 9 to the different components of the apparatus. The routines mentioned can be performed under the control of an external computer or manually.

Priming the apparatus may comprise drawing reaction components from each of the reservoirs to be used so that the conduits between the reservoirs and the selection valves are filled with the respective reaction component. This is desirable to increase accuracy in the amounts of reaction components delivered to the reaction vessel and reduces possibilities for contamination. In an embodiment, sampling the reaction mixture comprises removing a predetermined quantity of the reaction component to an external vessel or sensor during the course of a reaction. Return of the sample to the reaction vessel is possible in some cases. Harvesting may comprise withdrawing some or all of the reaction product at the end of a batch process or at an appropriate time in a continuous process. Rinsing may comprise rinsing used conduits and reservoirs with pure water. Cleaning the apparatus may comprise rinsing conduits and reservoirs with a cleaning solution.

In an embodiment of the invention, DNA template, at least one polymerase, one or more primers and nucleotides are added to a reaction vessel to form a reaction mixture. A part or portion of the reaction mixture is withdrawn from the reaction vessel and returned thereto in order to agitate the reaction mixture and ensure mixing thereof. At the end of the reaction, DNA is withdrawn from the reaction vessel. In an embodiment, the reaction mixture is withdrawn from a port provided at a lower part of the reaction vessel, preferably at the lowest point of the reaction vessel. In an embodiment, the part of the reaction mixture that is removed amounts to 50% or less of the whole reaction mixture, desirably 40% or less, preferably 30% or less. In an embodiment, the part of the reaction mixture that is removed amounts to 5% or more of the whole reaction mixture, desirably 10% or more, preferably 20% or more.

In an embodiment, the starting volume of the reaction mixture is between 10 ml and 10 litres, preferably 10 to 100 ml, 100 ml to 1000 ml or 1 to 10 litres.

The invention will now be described with reference to several non-limiting examples.

EXAMPLES

Materials and Methods

The DNA amplification carried out in the following examples was carried out using the Phi29 DNA polymerase acting on a ds circular template containing target sites for protelomerase TelN. The Phi29 polymerase produces long linear repeats of the circular template (concatamers) which can be processed with protelomerase TelN (Touchlight Genetics) into the desired closed linear DNA product. The creation of concatameric DNA by Phi29 DNA polymerase leads to an increase in the reaction viscosity due to their long length (reportedly up to 77 kilobases) while the processing of the double stranded concatameric DNA with protelomerase TelN leads to a decrease in viscosity because of their much shorter length (between 2 and 3 kilobases in the examples given).

Figure 2:
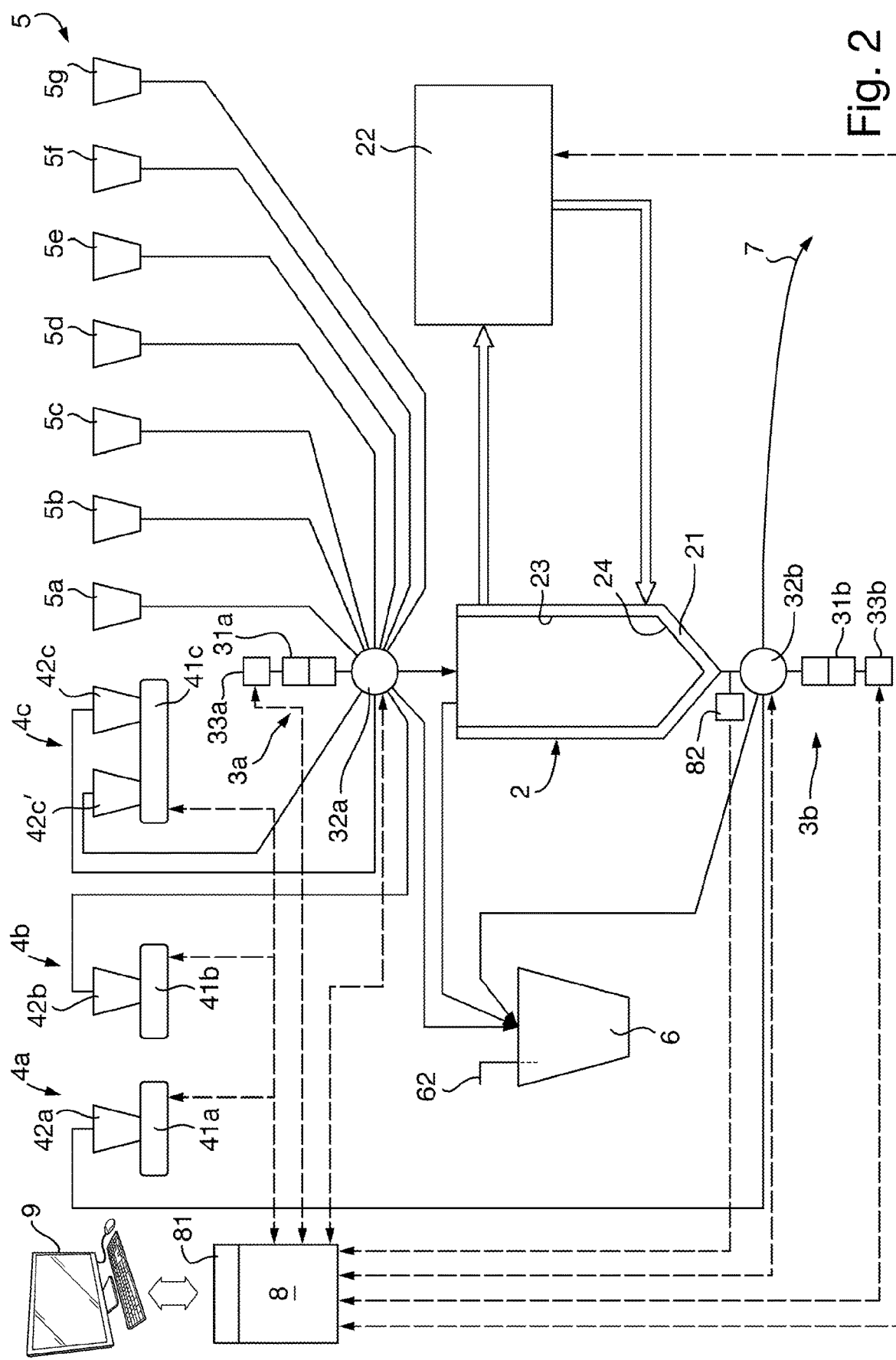
FIG. 2 is a schematic diagram of the apparatus of FIG. 1.

In Examples 1 and 3, DNA is produced in an apparatus as described herein, and with reference to FIGS. 1 to 3.

Example 1: On-Line Quantitation of DNA Produced in a Reaction from Pressure Differential Measurements First the apparatus was cleaned and decontaminated. Tubes were disconnected from the 10 reagent reservoirs (42a, 42b, 42c', 42c, 5a to 5g) and reconnected via Luer fittings to a 10 position manifold fed from a 120 ml reservoir containing 10% sodium hypochlorite solution. Similarly, a 60 ml reservoir of 10% sodium hypochlorite solution was attached to exit port 7 from selection valve 32b. By controlling the positions of the selection valves 32a and 32b and the actions of solenoids 33a and 33b on the 5 ml glass syringes 31a and 31b respectively, the whole system including the reaction vessel 2 itself was completely filled with sodium hypochlorite solution with no dead spaces. A minimum of 5 ml of solution was drawn through each tube. The reaction vessel (120 ml capacity) was heated to 50° C. by control action on thermocirculator 22 and the system maintained in this state for a period of 30 minutes. This procedure ensured that all contaminating DNA within all the feed tubes and the reaction vessel itself was completely destroyed.

Similarly, by using an appropriate program to control the selection valves and solenoids described above, the whole system was emptied of sodium hypochlorite solution by dispensing it into the waste vessel 6. Repeating above the process 5 times after replacing the sodium hypochlorite solution in the reservoirs with deionised water ensured the complete removal of any residual sodium hypochlorite from the whole system making it ready for use.

The tubes were then disconnected from the manifold reconnected to the 10 reagent reservoirs comprising sterile disposable polypropylene syringes with Luer lock fittings (5 ml to 20 ml capacity). Where indicated below, these syringes contained individual reaction components in a minimum volume of 2 ml. Otherwise they were left empty with the plungers fully depressed. Reservoir 5d consisted of two 60 ml syringes in parallel to give a total capacity of 120 ml of deionised water. In syringes containing reagents, air in each syringe barrel was expelled, after filling, by manually depressing the plunger until liquid just escaped from the syringe outlet. During this procedure, the syringe outlet was kept vertically above the syringe plunger to permit the expulsion of all the air in the barrel.

TABLE 1

Figure 9:
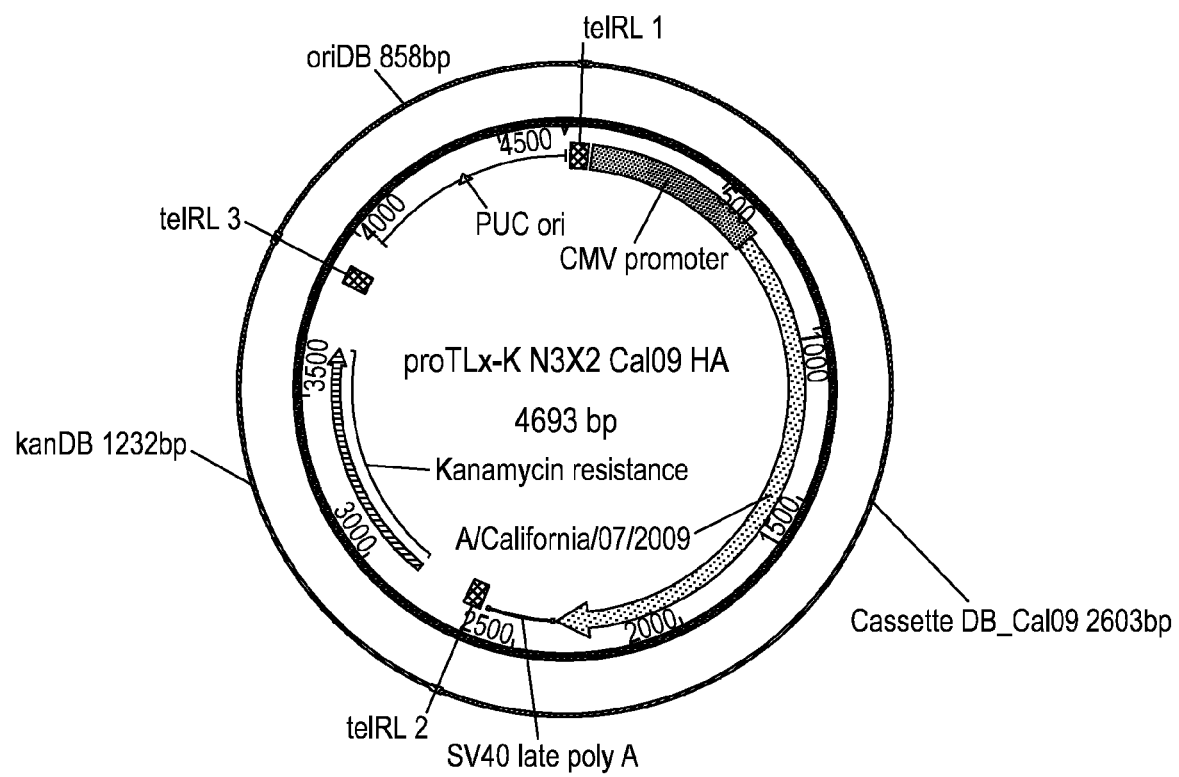
FIG. 9 depicts the proTLx-N3X2 Cal 09 HA DNA template.

| Addition order | Reservoir | Reservoir Temp ° C. | Reagent | Concentration | Volume dispensed | Concentration in reaction mixture |
|---|---|---|---|---|---|---|
| 1 | 5a | Room Temp | Circular DNA template proTLx-K N3X2 Cal09 HA (FIG. 9) (Touchlight Genetics) | 100 µg/ml | 7 ml | 7 µg/ml |
| 2 | 5b | Room Temp | Single oligonucleotide primer (11-mer) 5' gcgtataat*g*g 3' * phosphorothioate linkage (Oligo Factory) | 4.5 mM | 555 µl | 25 µM |
| 3 | 5c | Room Temp | NaOH | 1M | 1 ml | 10 mM |
| 4 | 5f | Room Temp | 10× Buffer 300 mM Tris-HCl, pH 7.5 300 mM KCl 75 mM $MgCl_2$ 50 mM $(NH_4)_2SO_4$ 20 mM DTT | | 10 ml | 30 mM Tris-HCl, pH 7.5 30 mM KCl 7.5 mM $MgCl_2$ 5 mM $(NH_4)_2SO_4$ 2 mM DTT |
| 5 | 42c | 4.0 | Phi 29 DNA polymerase (Touchlight Genetics) | 1 mg/ml | 1.2 ml | 12/µg/ml |
| 6 | 42c' | 4.0 | Pyrophosphatase (Enzymatics) | 4483 units/ml | 20 µl | 0.9 units/ml |
| 7 | 5e | Room Temp | dNTPs $Li^+$ salts (Bioline) | 100 mM | 2 ml | 2 mM (0.5 mM of each dNTP) |
| 8 | 5d | Room Temp | $H_2O$ | | 78.225 ml | |

The enzyme reagents, Phi29 DNA polymerase and pyrophosphatase, in reservoirs 42c and 42c' respectively, were maintained under stable conditions at 4° C. by temperature control device 41c. All other reagents were maintained at room temperature.

To achieve accurate dispensing of reagents into reaction vessel 2, the tubes between the reagent reservoirs and the selection valves 32a and 32b were primed by sequentially withdrawing very small amounts of the reagents and dispensing to waste vessel 6.

To denature the DNA template and bind the oligonucleotide primer, the reagents from reservoirs 5a, 5b and 5c were dispensed via selection valve 32a (by the action of solenoid 33a on syringe 31a) into a closed empty 5 ml syringe (reservoir 42b). The temperature of this reservoir was controlled by temperature control device 41b. Control action on 41b was used to raise its temperature to 95° C. for 3 minutes and then cool to 30° C. The combined reaction components in reservoir 42b were then dispensed into reaction vessel 2 via selection valve 32a. The remaining 5 reaction components were sequentially dispensed via selection valve 32a in the order show in Table 1 such that the final volume in reaction vessel 2 was 100 ml. The temperature of reaction vessel 2 was set at 30° C. by control action on thermocirculator 22. The reaction components were not exposed to surface temperatures greater than 2° C. above the set point.

Mixing of the reaction components was achieved by control action on the solenoid 33b and subsequently on the movement of mixing syringe 31b. The syringe action was controlled to withdraw from and return to the reaction vessel 2, 5 ml of reaction components. The mixing was discontinuous with the syringe activated for 1 minute at intervals of 29 minutes at a withdrawal/dispense rate of 55 ml/min.

The pressure change in the tubing between reaction vessel 2 and syringe 31b was measured by a vacuum and pressure sensor (Model PX409-2.5CGUSBH, Omega Engineering Limited, Manchester, M44 5BD, UK). This sensor measures pressure differences of −2.5 to +2.5 psi and was connected via a T-piece using a short section of ⅛ inch diameter PTFE tubing. The output signal from the sensor was monitored in real time and logged on the computer controlling the reactor using software supplier by the manufacturer. The reciprocating action of the mixing syringe produces an output of the pressure sensor that oscillates between positive and negative values (pull/push stroke of the mixing syringe). For each minute of pressure data recorded at each mixing time point, the minimum and maximum pressure readings were calculated for 3 sets of 20 seconds. The minimum value is subtracted from the maximum value for each set and an average calculated. With all other variables fixed such as syringe speed, tubing material, internal diameter and length and selection valve size and geometry any change in peak height could only be due to a change in viscosity of the reaction components. Very small pressure changes that might be attributed to environmental temperature and pressure fluctuations were not compensated for in pressure difference calculations. The first data point used for analysis was after approximately 45 minutes to ensure the system had fully equilibrated.

Figure 4:
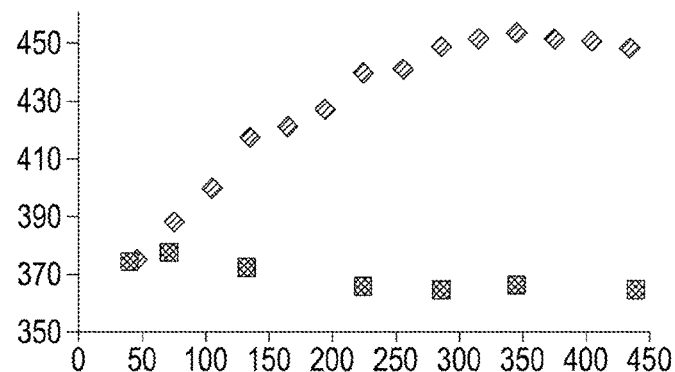
FIG. 4 is a graph showing data comparing the differential pressure data for a water-only control reaction (squares) with data generated from a standard DNA amplification reaction using Phi29 DNA polymerase (diamonds) against time (as described in Table 1). The pressure difference units are arbitrary and time is in minutes.

FIG. 4 clearly shows the increase in pressure difference with time for a DNA amplification reaction catalysed by Phi29 DNA polymerase. Samples taken from this reaction were also analysed directly for DNA using the Qubit™ BR dsDNA fluorometric assay (Life Technologies, Paisley, UK.). This assay measures double stranded DNA only. The concatameric DNA produced in the reaction was processed with protelomerase TelN to produce three covalently closed linear DNA molecules. The processed DNA was precipitated with PEG 8000 and NaCl at final concentrations of 5% and 2M respectively. The precipitated DNA was centrifuged at 14,000 g for 20 minutes and resuspended in an equivalent volume of nuclease-free deionised water.

Figure 5:
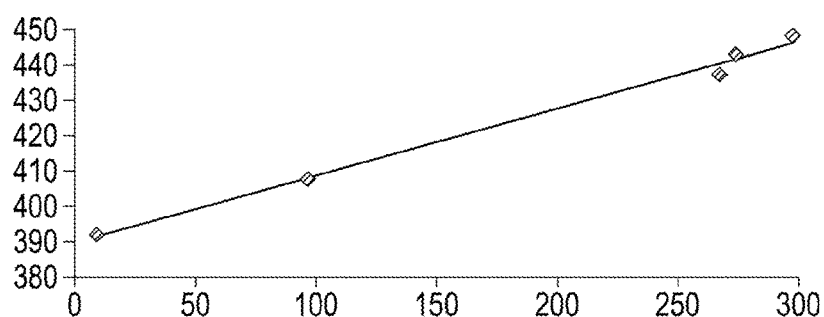
FIG. 5 is a plot of pressure difference versus DNA concentration measured by the Qubit® BR dsDNA fluorometric assay. The pressure difference units are arbitrary and the DNA concentration is in µg/ml.

FIG. 5 clearly shows that the increase in the pressure differential signal during the course of the reaction directly correlates with an increase in DNA concentration. The direct linear relationship between pressure and measured DNA also indicates that over this period of the reaction, the DNA exists predominantly in a double stranded form.

Example 2: Effect of Starting dNTP Concentrations on the Efficiency of their Incorporation into DNA In this experiment DNA amplification reactions (5 ml volumes) were conducted in 50 ml polypropylene centrifuge tubes. The components were sequentially added to the tubes in the order shown in Table 2 to give the indicated final concentrations. The effects of starting dNTP concentrations on DNA amplification were tested at 2 mM, 4 mM and 8 mM.

TABLE 2

Figure 10:
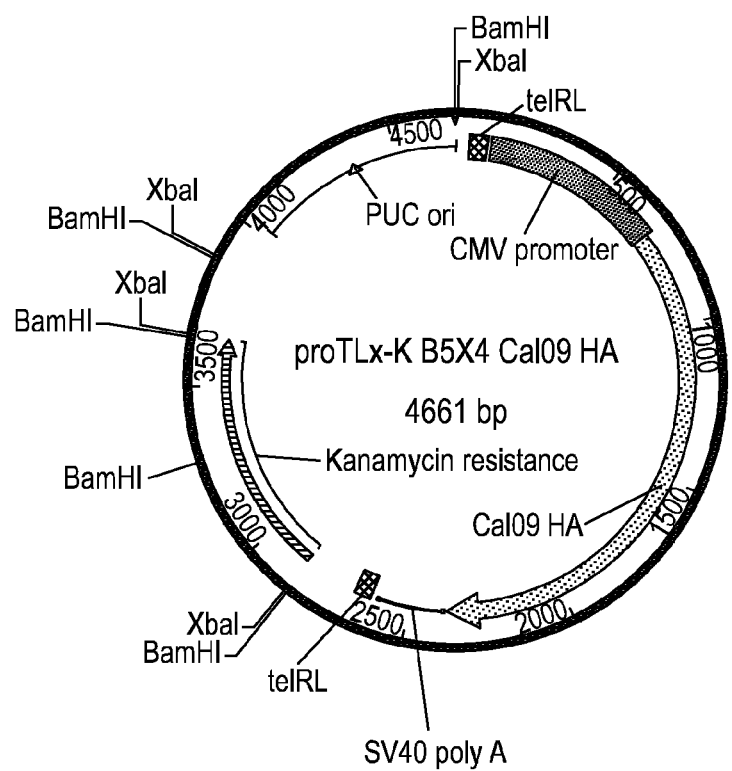
FIG. 10 depicts the proTLx B5X4 Cal 09 HA DNA template.

| Addition order | Reagent | Concentration in reaction mixture |
|---|---|---|
| 1 | Circular DNA template proTLx-K B5X4 Cal09 HA (Figure 10) (Touchlight Genetics) | 5 μg/ml |
| 2 | Single oligonucleotide primer (14-mer 5' atggrgcwattgt*g*t 3') r = a or g w = t or a * indicates phosphorothioate linkage (Oligo Factory) | 50 μM |
| 3 | $H_2O$ | To 5 ml |
| 4 | NaOH | 10 mM |
| 5 | dNTPs Li$^+$ salts (Bioline) | 2 mM 4 mM 8 mM |
| 6 | 10× Buffer 300 mM Tris-HCl, pH 7.5 300 mM KCl 75 mM $MgCl_2$ 50 mM $(NH_4)_2SO_4$ 20 mM DTT | 30 mM Tris-HCl, pH 7.5 30 mM KCl 7.5 mM $MgCl_2$ 5 mM $(NH_4)_2SO_4$ 2 mM DTT |
| 7 | Phi 29 DNA polymerase (Enzymatics) | 200 units/ml |
| 8 | Pyrophosphatase (Enzymatics) | 0.4 units/ml |

All tubes were incubated at 30° C. in an orbital incubator with minimal agitation for a period of 61.5 hours. This time period corresponded to approximately 10 times that required for completion of a DNA amplification reaction supplied with 2 mM dNTPs. At the end of the reaction, the concatameric DNA produced under each condition was processed with protelomerase TelN to produce two different covalently closed linear DNA molecules. The processed DNA was precipitated with PEG 8000 and NaCl at final concentrations of 5% and 2M respectively. The precipitated DNA was centrifuged at 14,000 g for 20 minutes and resuspended in 5 ml nuclease free deionised water. A sample of this DNA product was diluted 1 in 50 in deionised water and heated to 75° C. for 1 minute. A 10 μl sample of this diluted DNA was mixed with 2 μl of loading dye (Novel Juice, Newmarket Scientific Ltd., UK.) and a 10 μl sample applied to a 0.8% agarose gel and run under standard electrophoresis conditions until the DNA components were clearly separated (FIG. 6).

Figure 6:
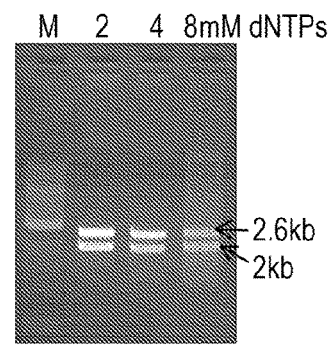
FIG. 6 is a photograph of an electrophoresis gel of covalently closed linear DNA products (2.6 kbases and 2 kbases) in a DNA amplification reaction with starting dNTP concentrations of 2 mM, 4 mM and 8 mM.

The electrophoresis gel in FIG. 6 clearly shows a dramatic decrease in product yield for the two covalently closed linear DNA products when the starting dNTP concentration was 8 mM. Since the reaction was carried out over a long time period, this indicates a very strong inhibitory effect on DNA amplification. Samples taken at the end of the reaction were also assayed for DNA using absorbance measurements at 260 nm and the results presented in Table 3.

TABLE 3

Concentrations of total processed DNA at the end of the reaction were calculated from absorbance measurements at 260 nm and expressed as a percentage of the maximum theoretical DNA yield from the different levels of dNTPs.

| Reaction dNTP (Li+ salts) concentration (mM) in reaction mixture | Maximum theoretical DNA yield (μg/ml) | Yield of DNA as percentage of the maximum theoretical yield (%) |
|---|---|---|
| 2 | 650 | 100 |
| 4 | 1300 | 85 |
| 8 | 2600 | 15 |

Table 3 confirms the electrophoresis results shown in FIG. 6 that starting dNTP concentrations in excess of 4 mM can dramatically reduce yields of DNA in Phi 29 DNA polymerase catalysed reactions. It was also apparent, that with a starting dNTP concentration of 8 mM, there was also a significant reduction in product purity evidenced by smearing around the two principal product bands (FIG. 6).

The observed reduction in DNA yield, by increasing the starting concentrations of dNTPs, can be attributed to a number of effects on the reaction. These include but are not limited to: substrate inhibition of the enzyme; Li+ or nucleotide effects on the stability of DNA strand interactions principally primer template interactions and/or the level of free $Mg^{2+}$ available for enzyme activity as a result of $Mg^{2+}$ binding to dNTPs. Inhibition of DNA amplification may be caused by a single factor or multiple factors functioning in a direct or indirect manner. Clearly, increasing the yield of DNA in the reaction to levels deemed acceptable for industrial production cannot be achieved simply by increasing the starting concentrations of dNTPs.

Example 3: Effect of Feeding dNTPs to a Phi29 DNA Polymerase Catalysed DNA Amplification Reaction Experiments were carried out to compare the effect of supplementing Phi29 catalysed DNA amplification reactions with additional amounts of dNTPs. Reactions were carried out as described in Example 1 but DNA concentrations were calculated from absorbance measurements at 260 nm. Comparisons were made between a reaction with 2 mM dNTPs and no-additional dNTPs added (Reaction 1), a reaction with 2 mM dNTPs and fed an additional 2 mM dNTPs at 530 mins (Reaction2), a reaction with 4 mM dNTPs from the start (no additional dNTPs added) and a reaction with 2 mM dNTPs fed 2 mM concentrations of additional dNTPs three times (at 500, 1430 and 4340 mins). The trigger for feeding any added dNTPs was a levelling off of the pressure differential signal. This activated the addition of an appropriate volume of dNTP solution from a reservoir such that the concentration of dNTPs in the reactor was increased by 2 mM.

Figure 7:
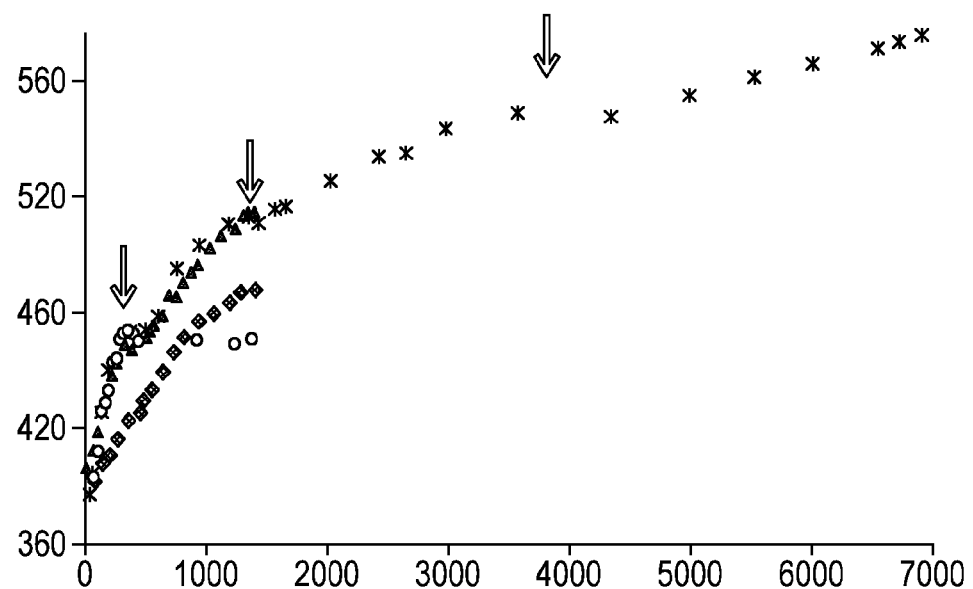
FIG. 7 is a plot of differential pressure measurements against time (minutes) for a reaction with a starting concentration of 2 mM dNTPs (no-additional dNTPs added)(open circles), 2 mM dNTPs fed an additional 2 mM dNTPs (triangles), 4 mM dNTPs from the start (no additional dNTPs added)(diamonds) and 2 mM dNTPs fed 2 mM concentration of additional dNTPs three times (crosses). Arrows indicate the times of dNTP addition for each reaction.

For each of these reaction conditions, a plot of pressure differential versus time is shown in FIG. 7.

From the data presented in FIG. 7, initial rates were calculated before, between and after dNTP addition as appropriate. These are shown in Table 4. Also, at the end of each reaction, the final yields of DNA were estimated and calculated as a percentage of the maximum theoretical yield from the concentration of dNTPs added. The data is shown in Table 5.

TABLE 4

Initial rates of DNA amplification for reactions 1 to 4 estimated from differential pressure measurements

| [dNTPs] mM | Reaction 1 2 mM dNTPs | Reaction 2 4 mM dNTPS | Reaction 3 2 mM dNTPs plus 1 addition of 2 mM dNTPs | Reaction 4 2 mM dNTPs plus 3 additions of 2 mM dNTPs | Metal cation: phosphate ratio for Reaction 4 $Mg^{2+}/PO_4^{3-}$ Ratio |
|---|---|---|---|---|---|
| | Initial rate of reaction (differential pressure units/min) | | | | |
| 2 | 0.3143 | | 0.2646 | 0.3588 | 1.25 |
| 4 | | 0.0761 | 0.0598 | 0.0593 | 0.625 |
| 6 | | | | 0.0226 | 0.417 |
| 8 | | | | 0.0135 | 0.313 |

TABLE 5

Final DNA yields for reactions 1 to 4 were calculated from absorbance measurements at 260 nm

| | Reaction 1 2 mM dNTPs | Reaction 2 4 mM dNTPS | Reaction 3 2 mM dNTPs plus 1 addition of 2 mM dNTPs | Reaction 4 2 mM dNTPs plus 3 additions of 2 mM dNTPs |
|---|---|---|---|---|
| Total [dNTP] mM | 2 | 4 | 4 | 8 |
| Final DNA yield (μg/ml) | 405 | 763 | 760 | 1400 |
| Yield of DNA as percentage of the maximum theoretical yield (%) | 62 | 59 | 58 | 54 |

Table 4 clearly shows that increasing the concentration of dNTPs dramatically reduces the rate at which at which DNA is amplified by Phi29 DNA polymerase. The effect on the reaction rate is cumulative and independent of when additional dNTPs are added.

In Example 2 it was shown that a reaction with a starting dNTP concentration of 8 mM produced only 15% of the maximum theoretical yield indicating an extremely slow reaction. In Table 5, a reaction in which 8 mM dNTPs are added in 2 mM aliquots (Reaction 4) achieves a DNA yield of 54% of the maximum theoretical yield which is a highly significant improvement. While gradual feeding of dNTPs appears to lead to a progressive reduction in reaction rate, the overall rate is faster and yields higher than introducing a high concentration of dNTPs at the start of the reaction.

Figure 8:
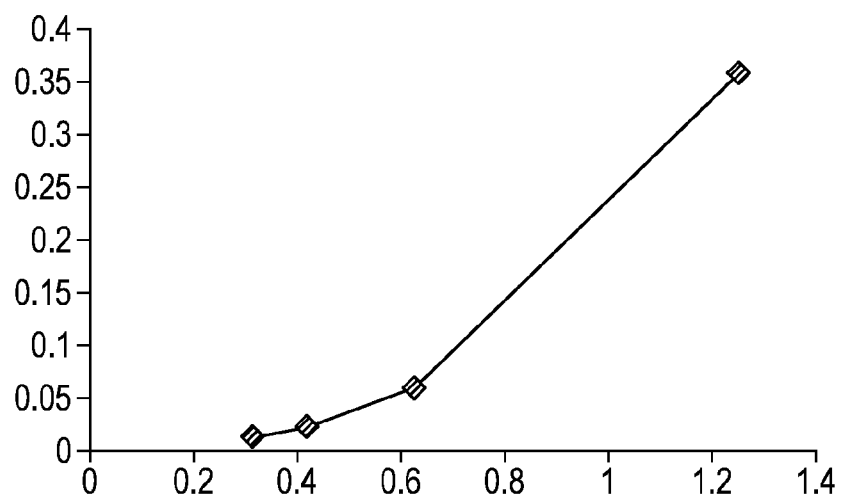
FIG. 8 is a plot of the initial reaction rate (differential pressure units/min) against the ratio of magnesium ions to dNTPs for a reaction with a starting concentration of 2 mM dNTPs fed an additional 3 times with 2 mM dNTPs.

Table 4 also shows that, in the process of feeding dNTPs, the molar ratio of $Mg^{2+}$ ions to dNTP phosphate groups ($Mg^{2+}/PO_4^{3-}$ ratio) reduces significantly and coincides with the observed decrease in reaction rate. This is illustrated in FIG. 8.

Thus feeding dNTPs can increase DNA production to industrially acceptable levels in enzyme catalysed reactions. However, to achieve higher reaction rates, it appears that the molar ratio of $Mg^{2+}$ ions to dNTP $PO_4^{3-}$ groups needs to be maintained at an optimal level by feeding $Mg^{2+}$ ions with the dNTPs.

Example 4: Effect of Magnesium Ion Concentration on the Efficiency of Incorporation of dNTPs into DNA In this experiment DNA amplification reactions (5 ml volumes) were conducted in 50 ml polypropylene centrifuge tubes. The components were pre-warmed to 30° C. and sequentially added to the tubes in the order shown in Table 6 to give the indicated final concentrations. Starting concentrations of $Mg^{2+}$ of 2.24 mM, 4.52 mM, 9 mM and 11.24 mM in combination with a starting dNTP concentration of 3 mM gave $Mg^{2+}/PO_4^{3-}$ ratios of 0.25, 0.5, 1 and 1.25 respectively. The tubes were incubated at 30° C. for 19 hours before further aliquots of dNTPs and $MgCl_2$ were added to increase the reaction concentration of dNTPs to 6 mM and the $Mg^{2+}$ concentrations to 4.48 mM, 9.04 mM, 18 mM and 22.48 mM to maintain $Mg^{2+}/PO_4^{3-}$ ratios of 0.25, 0.5, 1 and 1.25. The reaction was allowed to proceed for a further 24 hours at which time the DNA product as harvested and its concentration estimated. DNA was digested with a sufficient amount of protelomerase TelN and DNA was precipitated using 6% PEG 8000 in a buffer containing 500 mM NaCl, 100 mM $MgCl_2$. DNA was resuspended in a volume of 4 mls and DNA quantified using absorbance 260 nm measurements.

TABLE 6

Components of reaction mixture and order of addition.

Figure 11:
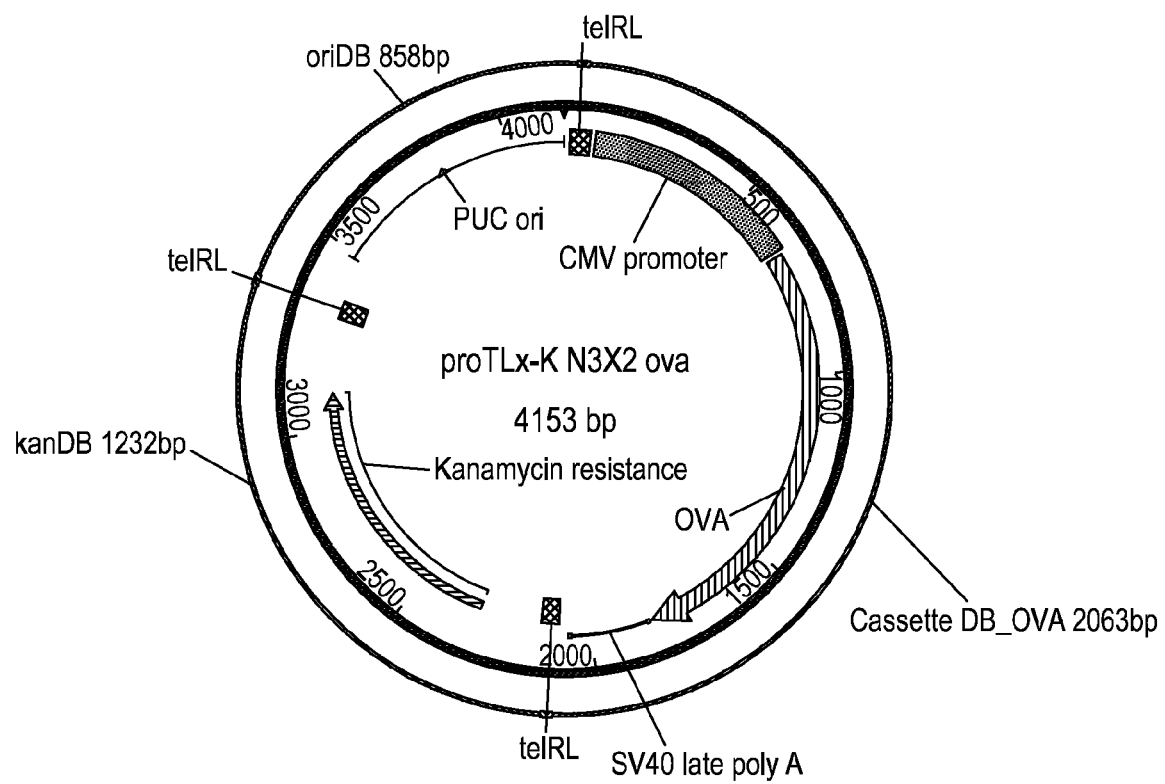
FIG. 11 depicts the proTLx-K N3X2 ova DNA template.
Figure 12:
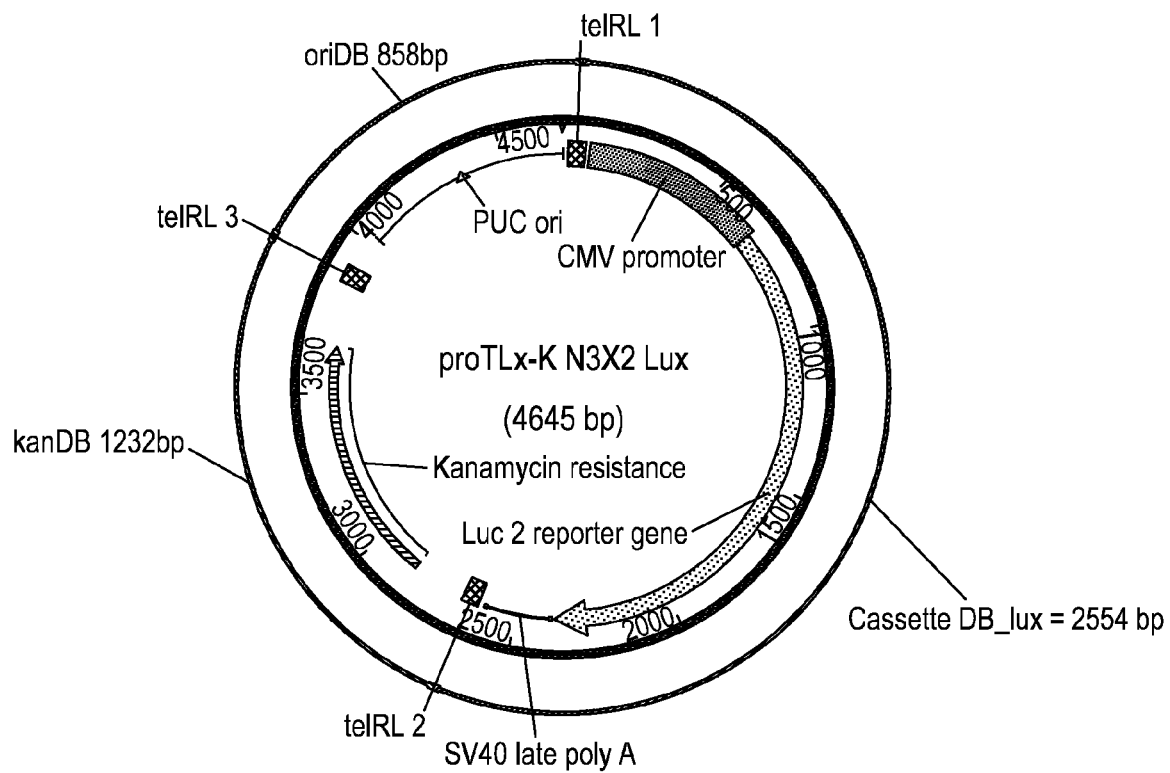
FIG. 12 depicts the proTLx-K N3X2 lux DNA template.

| Addition order | Reagent | Concentration in reaction mixture |
|---|---|---|
| 1 | Circular DNA template proTLx-K N3X2 ova (Figure 11) (Touchlight Genetics) | 2 µg/ml |
| 2 | Single oligonucleotide primer (11-mer) 5' gcgtataat*g*g 3' * phosphorothioate linkage (Oligo Factory) | 50 µM |
| 3 | $H_2O$ | To 5 ml |
| 4 | $MgCl_2$ | 2.24 mM<br>4.52 mM<br>9 mM<br>11.24 mM |
| 5 | NaOH | 2 mM |
| 6 | dNTPs<br>Li+ salts<br>(Bioline) | 3 mM |
| 7 | 10× Buffer<br>300 mM Tris-HCl, pH 7.9<br>300 mM KCl<br>50 mM $(NH_4)_2SO_4$<br>20 mM DTT<br>1% Tween-20 | 30 mM Tris-HCl, pH 7.9<br>30 mM KCl<br>5 mM $(NH_4)_2SO_4$<br>2 mM DTT<br>0.1% Tween™ 20 |
| 8 | Phi 29 DNA polymerase (Enzymatics) | 200 units/ml |
| 9 | Pyrophosphatase (Enzymatics) | 0.4 units/ml |

TABLE 7

DNA yields in reactions in dNTP fed reactions maintaining fixed $Mg^{2+}/PO_4^{3-}$ ratios

| Total $Mg^{2+}$ concentration (mM) | Total dNTP concentration (mM) | $Mg^{2+}/PO_4^{3-}$ Ratio | $Mg^{2+}/$ dNTP ratio | DNA Yield (mg) | DNA Yield (mg/mmole dNTPs) | % Max Theoretical Yield | DNA Concentration (g/l) |
|---|---|---|---|---|---|---|---|
| 4.48 | 6.0 | 0.25 | 0.75 | 2.67 | 89.0 | 27.4 | 0.53 |
| 9.04 | 6.0 | 0.50 | 1.5 | 5.40 | 180.0 | 55.4 | 1.08 |
| 18 | 6.0 | 1.00 | 3 | 5.49 | 183.1 | 56.3 | 1.10 |
| 22.48 | 6.0 | 1.25 | 3.75 | 4.77 | 159.0 | 48.9 | 0.95 |

The results in Table 7 show the effect of different $Mg^{2+}/PO_4^{3-}$ ratios on DNA yield after 43 hours in dNTP fed reactions. The lower DNA yield achieved after this time with a $Mg^{2+}/PO_4^{3-}$ ratio of 0.25 indicates a slower rate of reaction or inhibition of the reaction due to an insufficient concentration of $Mg^{2+}$ ions. Either way, the data indicates that there is an optimum $Mg^{2+}/PO_4^{3-}$ ratio that needs to be maintained for an efficient DNA amplification reaction for industrial use. The data indicates that the optimum ratio may be between 0.5 and 1.25. The data also indicates that if dNTPs are fed to a reaction, adding additional $Mg^{2+}$ ions maintain an optimum $Mg^{2+}/PO_4^{3-}$ ratio (ideally 1) allows efficient conversion into DNA.

Figure 13:
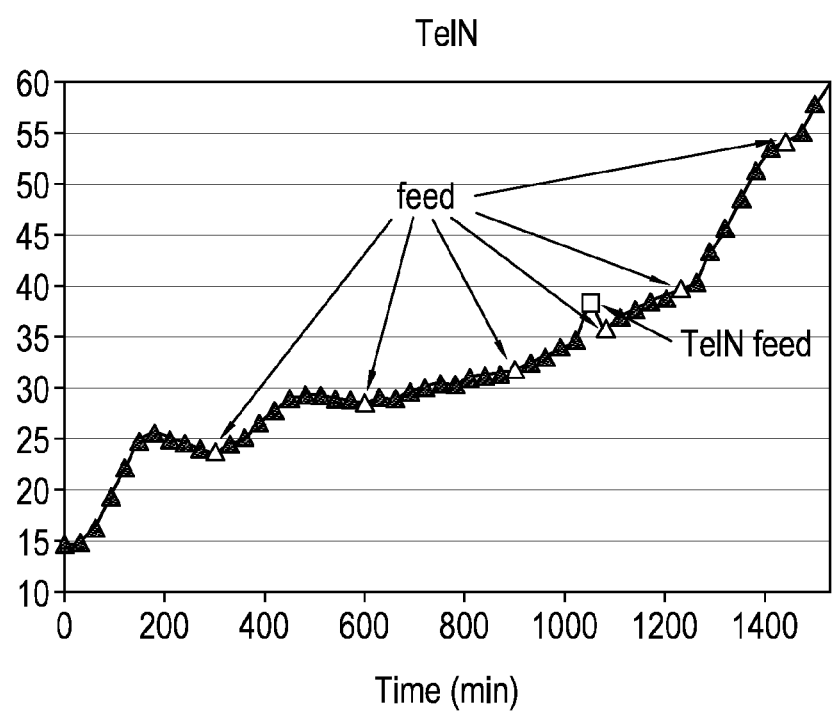
FIG. 13 depicts a plot of differential pressure measurements against time (minutes) for a reaction initially containing 2 mM dNTPs and 7.5 mM $Mg^{2+}$, that had a controlled addition ("Feed") of nucleotides and $Mg^{2+}$ at the points indicated (300 mins, 600 mins, 900 mins, 1080 mins, 1230 mins and 1440 mins—white triangles) with 2 mM dNTPs and sufficient $Mg^{2+}$ to maintain a ratio of 3:1 $Mg^{2+}$: dNTPS after the first feed), to which a controlled addition of a protelomerase is made at at 1050 mins (2 µM TelN) as indicated (square). Arrows indicate the time of each dNTP addition immediately followed by addition of $Mg^{2+}$, and addition of TelN.

Example 5: Effect of Protelomerase TelN Addition on Phi29 DNA Polymerase Catalysed DNA Amplification Reaction Fed with Multiple Aliquots of dNTPs Experiments were carried out to compare the effect of supplementing Phi29 catalysed DNA amplification reactions on the plasmid ProTLx-K N3X2 Lux (FIG. 13), with additional amounts of dNTPs and the protelomerase TelN. Reactions were essentially carried out as described in Example 1 but with reservoir 42b containing a 25 µM TelN solution in 12 mM Tris-HCl (pH7.4), 90 mM NaCl, 0.1 mM EDTA. 1 mM DTT, 50% Glycerol maintained at 4° C. and reservoir 5g containing 100 mM $MgCl_2$ solution in deionised water. The starting concentration of template ProTLx-K_N3X2 Lux was 5 µg/ml.

Following the batch phase of the reaction, aliquots of dNTPs were added to the reaction vessel 2, via syringe 31a, to achieve an increase in concentration of 2 mM at selected time intervals of 300 mins, 600 mins, 900 mins, 1080 mins, 1230 mins and 1440 mins. At the same time intervals and immediately after the addition of the dNTPs, aliquots of $MgCl_2$ were added to achieve a 3:1 ratio of $[Mg^{2+}]:[dNTPs]$. At 1050 mins, protelomerase TelN was dispensed into the reaction vessel 2 give a final concentration of 2 µM.

Following the initial batch phase of the reaction (up to 300 min), there is a steady increase in the differential pressure measurement corresponding to concatameric DNA synthesis. Following the addition of protelomerase TelN to the reaction at 1050 mins there is a 3.6 fold increase in the rate of the pressure change corresponding to a dramatic increase in DNA synthesis. It is proposed that the single addition of TelN during the dNTP/$Mg^{2+}$ fed phase of the reaction leads to the production of closed linear DNA which can act as a template for further DNA amplification. The further feeding of $Mg^{2+}$/dNTPs after this point is critical to ensure the observed increased rate of DNA synthesis.

The invention claimed is:

1. A cell-free process for synthesising DNA comprising contacting a DNA template with at least one polymerase in the presence of nucleotides to form a reaction mixture, wherein the DNA template is amplified by strand displacement replication, and wherein further nucleotides are supplied to the reaction mixture continuously or at intervals during the process.

2. A process according to claim 1 wherein said reaction mixture further comprises one or more primers.

3. A cell-free process for synthesising DNA comprising contacting a DNA template with at least one polymerase in the presence of nucleotides and at least one primer to form a reaction mixture, wherein the DNA template is amplified by strand displacement replication, and wherein further nucleotides are supplied to the reaction mixture continuously or at intervals during the process.

4. A cell-free process for synthesising DNA according to claim 1, wherein the reaction mixture further comprises one or more metal cations and further metal cations are supplied to the reaction mixture continuously or at intervals during the process.

5. The process according to claim 4 wherein said further nucleotides and further metal cations are supplied independently to the reaction mixture.

6. The process according to claim 1 wherein said DNA template is circular, and amplification of said DNA template is by rolling circle amplification.

7. The process according claim 1, wherein said DNA template is a closed linear DNA.

8. The process according to claim 1 wherein said DNA template comprises at least one processing enzyme target sequence.

9. The process according to claim 8 wherein a processing enzyme is supplied at regular or irregular intervals during the process to the reaction mixture.

10. The process according to claim 1 wherein said further nucleotides are supplied in a plurality of aliquots to the reaction mixture.

11. The process according to claim 1 wherein said further nucleotides are supplied as aliquots at regular intervals throughout the duration of the process, optionally at least every 30 minutes.

12. The process according to claim 4 wherein said metal cations are supplied as aliquots at regular intervals throughout the duration of the process, optionally at least every 30 minutes.

13. The process according to claim 11 wherein at least 3, 4, 5, 6, 7, 8, 9 or 10 aliquots are supplied to the reaction mixture.

14. The process according to claim 10 wherein said aliquots are fed from an external source using a pump or are supplied to the reaction mixture by use of an osmotic pump.

15. The process according to claim 1 wherein said nucleotides or further nucleotides comprise biologically inactive nucleotides.

16. The process according to claim 1 wherein said further nucleotides are supplied in response to a signal related to the concentration of DNA in the reaction mixture.

17. The process according to claim 16 wherein the signal indicating the concentration of DNA is generated by measuring a pressure difference created by a reciprocating pump that removes and returns a portion of the reaction mixture, optionally over a pressure sensor.

18. The process according claim 1 wherein said process is performed in a synthesis apparatus, said apparatus comprising:
 a reaction vessel having at least a first port and a second port;
 a temperature control device for controlling the temperature of the reaction vessel;
 a plurality of reservoirs for holding reaction components;
 a plurality of conduits, each of the plurality of conduits connecting the first port of the reaction vessel with a respective one of the plurality of reservoirs;
 at least one pressure sensor located proximate the first port or second port of the reaction vessel;
 supply means for selectively supplying controlled amounts of reaction components held in the reservoirs to the reaction vessel;
 agitation means for selectively withdrawing an amount of content from the reaction vessel through the second port thereof and selectively returning the contents of the reaction vessel to the reaction vessel through the second port thereof; and
 control means for controlling the supply means and the agitation means,
wherein, the pressure sensor detects a change in pressure externally of the reaction vessel and sends a signal to the control means and the control means controls the supply means and/or agitation means in response to a change in observed pressure.

19. The process according to claim 18 wherein said reaction components comprise said further nucleotides and/or metal cations.

20. The process according to claim 4 wherein said metal cations comprise one or more metals selected from the list consisting of: magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), lithium ($Li^+$), sodium ($Na^+$) and potassium ($K^+$).

21. The process according to claim 4, wherein said metal cation is a divalent cation and the ratio between said divalent metal cations and the nucleotides is maintained at about 3:1 in the reaction mixture.

22. The process according to claim 1 wherein the concentration of nucleotides in the reaction mixture is maintained between 0.001 mM and 6 mM, optionally at about 3 mM.

23. The process according to claim 1 wherein said nucleotides and/or further nucleotides are deoxyribonucleoside triphosphates (dNTPs), or a derivative or modified version thereof.

24. The process according to claim 1 wherein said nucleotides and/or further nucleotides are one or more of deoxyadenosine triphosphate (dATP), deoxyguanosine triphosphate (dGTP), deoxycytidine triphosphate (dCTP), deoxythymidine triphosphate (dTTP) and derivatives thereof.

25. The process according to claim 1 wherein said nucleotides are provided as one or more of free acids, their salts or chelates thereof, optionally wherein said salts or chelates includes one or more of the following metal ions: $Mg^{2+}$, $Be^{2+}$, $Ca^{2+}$, $Sr^{2+}$, $Li^+$, $Na^+$, $K^+$, $Mn^{2+}$ or $Zn^{2+}$.

26. The process according to claim 8 wherein said processing enzyme is supplied in response to a signal related to the concentration of the DNA in the reaction mixture.

27. The process according to claim 20, wherein said metal cations comprise $Mg^{2+}$.

28. The process of claim 7, wherein said DNA template is incubated under denaturing conditions to form a closed circular single stranded DNA.

29. The process according to claim 8, wherein the at least one processing enzyme target sequence comprises a recombinase targeting sequence or a protelomerase target sequence.

30. The method of claim 15, wherein said nucleotides or further nucleotides are supplied to the reaction mixture via activation.

31. The method of claim 16, wherein the concentration of the DNA in the reaction mixture is monitored by measuring the difference in pressure of the reaction mixture, or a portion thereof, which can optionally generate a signal.

* * * * *